(12) United States Patent
Chu et al.

(10) Patent No.: US 11,854,688 B2
(45) Date of Patent: Dec. 26, 2023

(54) SEMICONDUCTOR DEVICE AND METHOD

(71) Applicant: Taiwan Semiconductor Manufacturing Co., Ltd., Hsinchu (TW)

(72) Inventors: Feng-Ching Chu, Pingtung County (TW); Wei-Yang Lee, Taipei (TW); Feng-Cheng Yang, Zhudong Township (TW); Yen-Ming Chen, Chu-Pei (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 16/888,264

(22) Filed: May 29, 2020

(65) Prior Publication Data

US 2021/0257260 A1 Aug. 19, 2021

Related U.S. Application Data

(60) Provisional application No. 62/978,617, filed on Feb. 19, 2020.

(51) Int. Cl.
*H01L 21/762* (2006.01)
*H01L 21/8234* (2006.01)
(Continued)

(52) U.S. Cl.
CPC ........... *G16H 40/20* (2018.01); *G06Q 50/163* (2013.01); *G16H 40/63* (2018.01);
(Continued)

(58) Field of Classification Search
CPC ........... H01L 21/845; H01L 21/823418; H01L 21/823431; H01L 21/823462;
(Continued)

(56) References Cited

U.S. PATENT DOCUMENTS

| 5,908,313 A | * | 6/1999 | Chau | H01L 29/41783 |
| | | | | 257/E21.345 |
| 7,361,563 B2 | * | 4/2008 | Shin | H01L 29/7834 |
| | | | | 257/E29.267 |

(Continued)

FOREIGN PATENT DOCUMENTS

| CN | 103871850 | * | 6/2014 | ....... H01L 21/02046 |
| CN | 108615731 | * | 10/2018 | ......... H01L 21/0928 |

(Continued)

*Primary Examiner* — Mary A Wilczewski
(74) *Attorney, Agent, or Firm* — Slater Matsil, LLP

(57) ABSTRACT

Methods for performing a pre-clean process to remove an oxide in semiconductor devices and semiconductor devices formed by the same are disclosed. In an embodiment, a method includes forming a shallow trench isolation region over a semiconductor substrate; forming a gate stack over the shallow trench isolation region; etching the shallow trench isolation region adjacent the gate stack using an anisotropic etching process; and after etching the shallow trench isolation region with the anisotropic etching process, etching the shallow trench isolation region with an isotropic etching process, process gases for the isotropic etching process including hydrogen fluoride (HF) and ammonia ($NH_3$).

20 Claims, 23 Drawing Sheets

(51) Int. Cl.

| | |
|---|---|
| *H01L 27/088* | (2006.01) |
| *H01L 29/66* | (2006.01) |
| *H01L 21/8238* | (2006.01) |
| *G16H 40/20* | (2018.01) |
| *G16H 40/63* | (2018.01) |
| *H04L 9/40* | (2022.01) |
| *G06Q 50/16* | (2012.01) |
| *G06Q 10/20* | (2023.01) |

(52) U.S. Cl.
CPC ............... *H01L 21/76224* (2013.01); *H01L 21/823418* (2013.01); *H01L 21/823431* (2013.01); *H01L 21/823462* (2013.01); *H01L 21/823481* (2013.01); *H01L 21/823807* (2013.01); *H01L 27/0886* (2013.01); *H01L 29/66795* (2013.01); *H04L 63/0876* (2013.01); *G06Q 10/20* (2013.01); *H01L 21/823821* (2013.01); *H01L 29/66545* (2013.01)

(58) Field of Classification Search
CPC ..... H01L 21/823481; H01L 21/823807; H01L 21/823814; H01L 21/823821; H01L 21/823828; H01L 21/823864; H01L 21/823871; H01L 21/823878; H01L 21/76224; H01L 21/76829; H01L 21/3065; H01L 21/31116; H01L 27/0886; H01L 27/0924; H01L 27/1211; H01L 29/41791; H01L 29/66545; H01L 29/66795; H01L 29/785
See application file for complete search history.

(56) References Cited

U.S. PATENT DOCUMENTS

| | | | |
|---|---|---|---|
| 7,592,231 B2 * | 9/2009 | Cheng | H01L 29/7834 438/300 |
| 8,754,448 B2 * | 6/2014 | Liao | H01L 27/088 117/22 |
| 8,900,942 B2 * | 12/2014 | Kim | H01L 27/088 438/300 |
| 9,209,247 B2 | 12/2015 | Colinge et al. | |
| 9,236,267 B2 | 1/2016 | De et al. | |
| 9,343,370 B1 | 5/2016 | Lee et al. | |
| 9,412,817 B2 | 8/2016 | Yang et al. | |
| 9,412,828 B2 | 8/2016 | Ching et al. | |
| 9,460,968 B2 | 10/2016 | Lin et al. | |
| 9,472,618 B2 | 10/2016 | Oxland | |
| 9,502,265 B1 | 11/2016 | Jiang et al. | |
| 9,520,482 B1 | 12/2016 | Chang et al. | |
| 9,536,738 B2 | 1/2017 | Huang et al. | |
| 9,576,814 B2 | 2/2017 | Wu et al. | |
| 9,608,116 B2 | 3/2017 | Ching et al. | |
| 9,842,778 B2 | 12/2017 | You et al. | |
| 11,088,245 B2 | 8/2021 | Chu et al. | |
| 11,183,570 B2 | 11/2021 | Singh et al. | |
| 2003/0186526 A1 * | 10/2003 | Chang | H01L 21/76831 438/600 |
| 2004/0058500 A1 * | 3/2004 | Lee | H01L 21/28518 257/E21.228 |
| 2005/0279997 A1 * | 12/2005 | Shin | H01L 29/66628 438/300 |
| 2007/0235763 A1 * | 10/2007 | Doyle | H01L 29/78687 257/E29.28 |
| 2008/0171438 A1 * | 7/2008 | Sinha | H01L 21/823481 438/689 |
| 2009/0166704 A1 * | 7/2009 | Higashitani | H01L 27/11521 257/E21.422 |
| 2010/0032715 A1 * | 2/2010 | Cheng | H01L 29/6653 257/190 |
| 2010/0109045 A1 | 5/2010 | Liu et al. | |
| 2010/0216296 A1 | 8/2010 | Muraki et al. | |
| 2010/0224938 A1 * | 9/2010 | Zhu | H01L 29/165 438/285 |
| 2010/0240218 A1 * | 9/2010 | Ugajin | H01L 21/67069 156/345.52 |
| 2011/0207323 A1 * | 8/2011 | Ditizio | H01L 21/02271 257/E21.597 |
| 2011/0318903 A1 * | 12/2011 | Fishburn | H01L 21/76229 257/E21.546 |
| 2012/0241815 A1 * | 9/2012 | Kim | H01L 29/45 257/190 |
| 2014/0061794 A1 * | 3/2014 | Cheng | H01L 29/7849 257/E27.111 |
| 2014/0353741 A1 * | 12/2014 | Montanini | H01L 21/28123 438/300 |
| 2015/0255607 A1 | 9/2015 | Lim et al. | |
| 2018/0040615 A1 * | 2/2018 | Chang | H01L 21/823431 |
| 2018/0175046 A1 * | 6/2018 | Chiou | H01L 29/7848 |
| 2019/0103324 A1 * | 4/2019 | Perng | H01L 21/28202 |
| 2019/0148151 A1 * | 5/2019 | Okuno | H01L 29/66545 257/401 |
| 2020/0043927 A1 | 2/2020 | Wang et al. | |
| 2020/0381537 A1 * | 12/2020 | Lin | H01L 29/66795 |
| 2021/0013306 A1 | 1/2021 | Choi et al. | |
| 2021/0257260 A1 * | 8/2021 | Chu | H01L 21/823431 |

FOREIGN PATENT DOCUMENTS

| | | | | |
|---|---|---|---|---|
| KR | 20100028435 A | | 3/2010 | |
| KR | 10-2010-0095398 | * | 8/2010 | ............ C30B 25/08 |
| KR | 20140111577 A | | 9/2014 | |
| KR | 20150105866 A | | 9/2015 | |
| KR | 20160064936 A | | 6/2016 | |
| KR | 20160102787 A | | 8/2016 | |
| KR | 20190049329 A | | 5/2019 | |
| KR | 20190058325 A | | 5/2019 | |
| KR | 20200000093 A | | 1/2020 | |
| WO | WO 01/93311 | * | 12/2001 | ....... H01L 21/76237 |

* cited by examiner

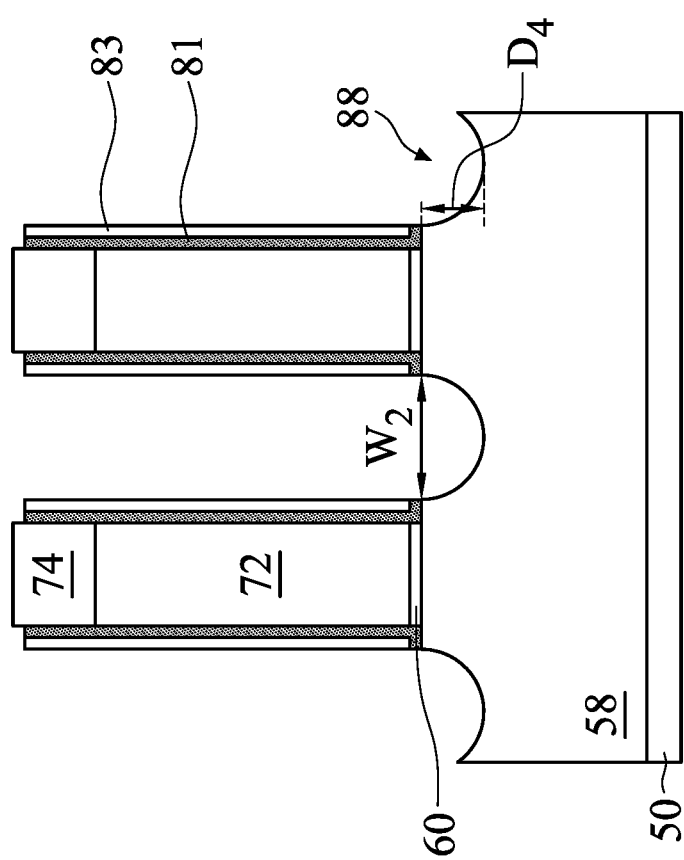

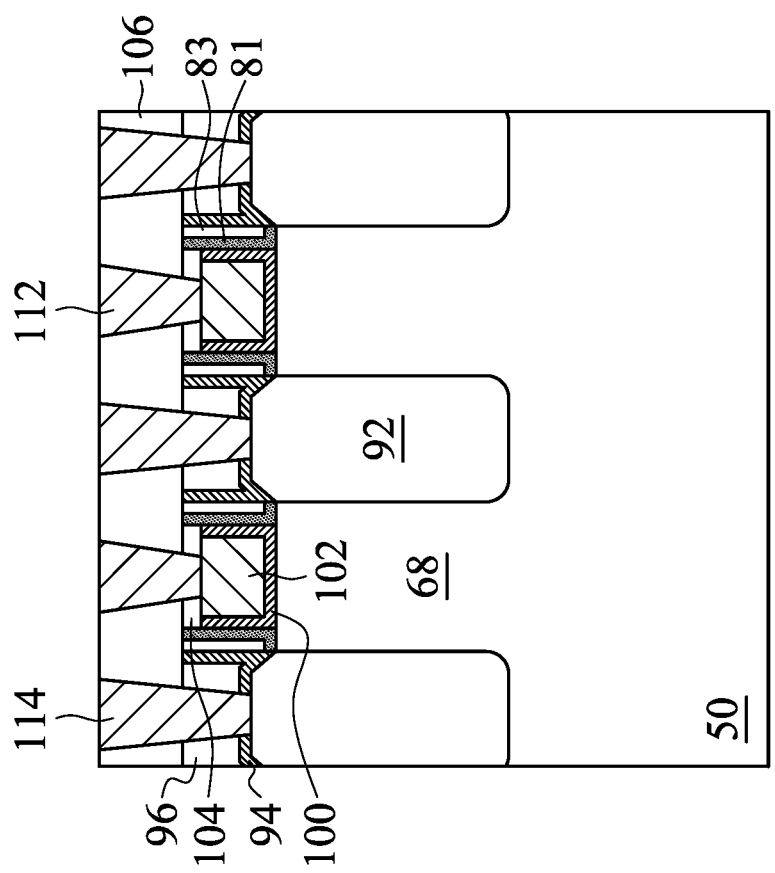
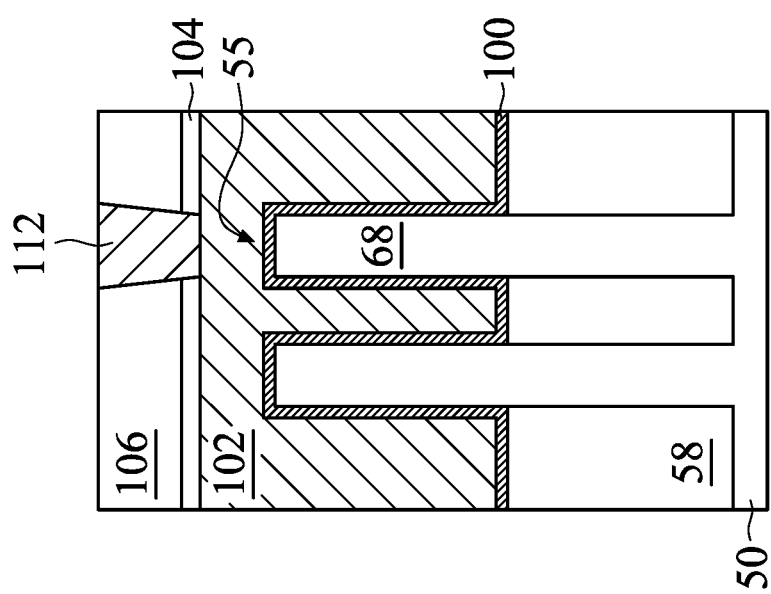
Figure 17A
Figure 17B

SEMICONDUCTOR DEVICE AND METHOD

PRIORITY CLAIM AND CROSS-REFERENCE

This application claims the benefit of U.S. Provisional Application No. 62/978,617, filed on Feb. 19, 2020 which application is hereby incorporated herein by reference.

BACKGROUND

Semiconductor devices are used in a variety of electronic applications, such as, for example, personal computers, cell phones, digital cameras, and other electronic equipment. Semiconductor devices are typically fabricated by sequentially depositing insulating or dielectric layers, conductive layers, and semiconductor layers of material over a semiconductor substrate, and patterning the various material layers using lithography to form circuit components and elements thereon.

The semiconductor industry continues to improve the integration density of various electronic components (e.g., transistors, diodes, resistors, capacitors, etc.) by continual reductions in minimum feature size, which allow more components to be integrated into a given area.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 2, 3, 4, 5, 6A, 6B, 7A, 7B, 8A, 8B, 9A, 9B, 9C, 10A, 10B, 10C, 11A, 11B, 11C, 12A, 12B, 12C, 12D, 13A, 13B, 14A, 14B, 15A, 15B, 15C, 16A, 16B, 17A, 17B, 17C, and 17D are cross-sectional views of intermediate stages in the manufacturing of semiconductor devices, in accordance with some embodiments.

DETAILED DESCRIPTION

Figure 1:
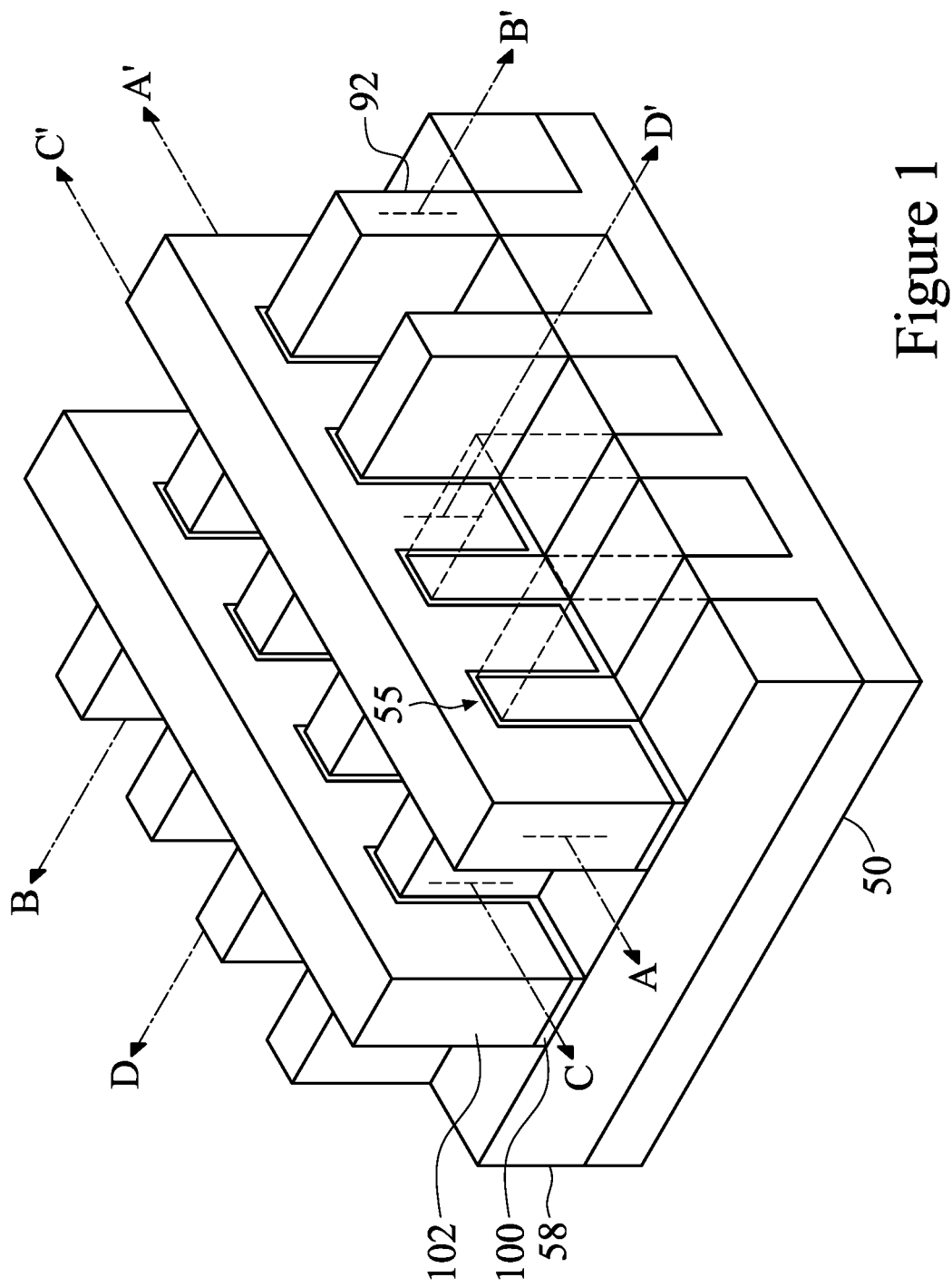
FIG. 1 illustrates an example of a semiconductor device including fin field-effect transistors (FinFETs) in a three-dimensional view, in accordance with some embodiments.

The following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Various embodiments provide methods of performing an improved pre-clean process for removing a native oxide layer in semiconductor devices and semiconductor devices formed by said methods. The pre-clean process may be a plasma-less dry etching process. In some embodiments, the pre-clean process may use etchants such as hydrogen fluoride (HF) and ammonia ($NH_3$) to remove an oxide (e.g., a native oxide) from recesses formed in fins before forming the epitaxial source/drain regions in the fins. Performing the pre-clean process using the plasma-less dry etch process may reduce the removal of material from shallow trench isolation (STI) regions and provide better STI region profiles. This may result in semiconductor devices formed by methods including the pre-clean process having increased breakdown voltage, better performance, and reduced device defects.

FIG. 1 illustrates an example of FinFETs, in accordance with some embodiments. The FinFETs comprise fins 55 on a substrate 50 (e.g., a semiconductor substrate). STI regions 58 are disposed in the substrate 50, and the fins 55 protrude above and from between neighboring STI regions 58. Although the STI regions 58 are described/illustrated as being separate from the substrate 50, as used herein the term "substrate" may be used to refer to just the semiconductor substrate or a semiconductor substrate inclusive of STI regions. Additionally, although the fins 55 are illustrated as single, continuous materials with the substrate 50, the fins 55 and/or the substrate 50 may comprise a single material or a plurality of materials. In this context, the fins 55 refer to the portions extending between the neighboring STI regions 58.

Gate dielectric layers 100 are along sidewalls and over a top surface of the fins 55, and gate electrodes 102 are over the gate dielectric layers 100. Epitaxial source/drain regions 92 are disposed on opposite sides of the fins 55, the gate dielectric layers 100, and the gate electrodes 102. FIG. 1 further illustrates reference cross-sections that are used in later figures. Cross-section A-A' is along a longitudinal axis of a gate electrode 102 and in a direction, for example, perpendicular to the direction of current flow between the epitaxial source/drain regions 92 of the FinFETs. Cross-section B-B' is perpendicular to cross-section A-A' and is along a longitudinal axis of a fin 55 and in a direction of, for example, the current flow between the epitaxial source/drain regions 92 of the FinFETs. Cross-section C-C' is parallel to cross-section A-A' and extends through the epitaxial source/drain regions 92 of the FinFETs. Cross-section D-D' is parallel to cross-section B-B' and extends through the fins 55 of the FinFETs. Subsequent figures refer to these reference cross-sections for clarity.

Some embodiments discussed herein are discussed in the context of fin field effect transistors (FinFETs) formed using gate-last processes. In some embodiments, a gate-first process may be used. Also, some embodiments contemplate aspects used in planar devices, such as planar FETs, nanostructure (e.g., nanosheet, nanowire, gate-all-around, or the like) field effect transistors (NSFETs), or the like.

FIGS. 2 through 17D are cross-sectional views of intermediate stages in the manufacturing of FinFETs, in accordance with some embodiments. FIGS. 2 through 5 illustrate reference cross-section A-A' illustrated in FIG. 1. FIGS. 6A, 12A, 13A, 14A, 15A, 16A, and 17A are illustrated along reference cross-section A-A' illustrated in FIG. 1. FIGS. 6B, 7B, 8B, 9B, 10B, 11B, 12B, 13B, 14B, 15B, 15C, 16B, and 17B are illustrated along a similar cross-section B-B' illustrated in FIG. 1. FIGS. 7A, 8A, 9A, 10A, 11A, 11C, and 12C are illustrated along reference cross-section C-C' illustrated in FIG. 1. FIGS. 9C, 10C, 12D, 17C, and 17D are illustrated along reference cross-section D-D' illustrated in FIG. 1.

Figure 2:
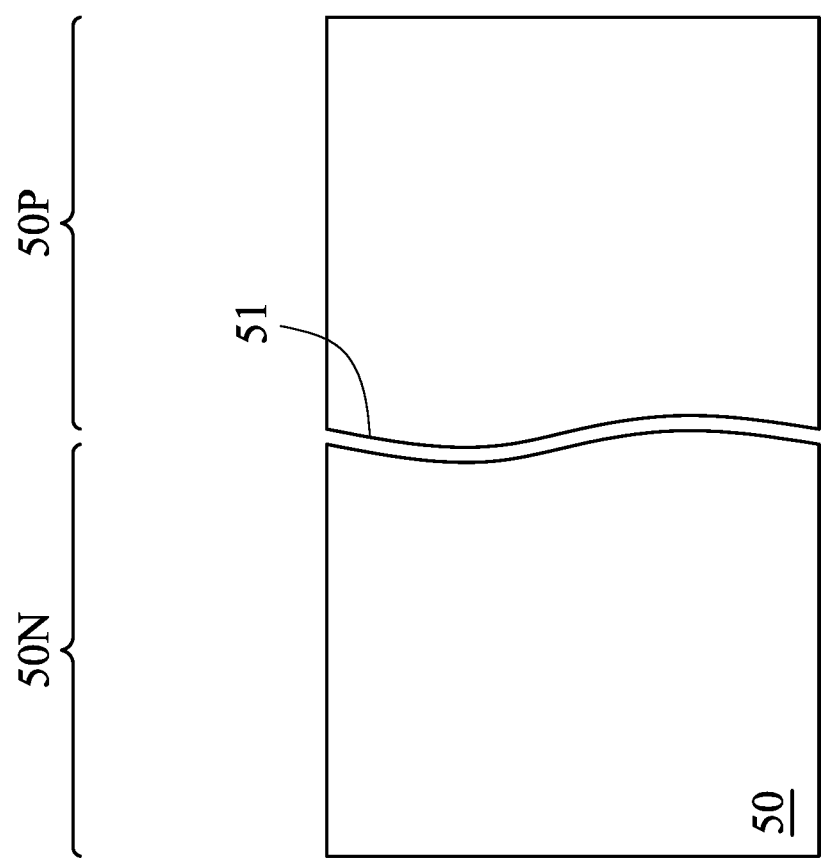

In FIG. 2, a substrate 50 is provided. The substrate 50 may be a semiconductor substrate, such as a bulk semiconductor, a semiconductor-on-insulator (SOI) substrate, or the like, which may be doped (e.g., with a p-type or an n-type dopant) or undoped. The substrate 50 may be a wafer, such as a silicon wafer. Generally, an SOI substrate is a layer of a semiconductor material formed on an insulator layer. The insulator layer may be, for example, a buried oxide (BOX) layer, a silicon oxide layer, or the like. The insulator layer is provided on a substrate, typically a silicon or glass substrate. Other substrates, such as a multi-layered or gradient substrate may also be used. In some embodiments, the semiconductor material of the substrate 50 may include silicon; germanium; a compound semiconductor including silicon carbide, gallium arsenide, gallium phosphide, indium phosphide, indium arsenide, and/or indium antimonide; an alloy semiconductor including silicon-germanium, gallium arsenide phosphide, aluminum indium arsenide, aluminum gallium arsenide, gallium indium arsenide, gallium indium phosphide, and/or gallium indium arsenide phosphide; or combinations thereof.

The substrate 50 has a region 50N and a region 50P. The region 50N can be for forming n-type devices, such as NMOS transistors, e.g., n-type FinFETs. The region 50P can be for forming p-type devices, such as PMOS transistors, e.g., p-type FinFETs. The region 50N may be physically separated from the region 50P (as illustrated by divider 51), and any number of device features (e.g., other active devices, doped regions, isolation structures, etc.) may be disposed between the region 50N and the region 50P.

Figure 3:
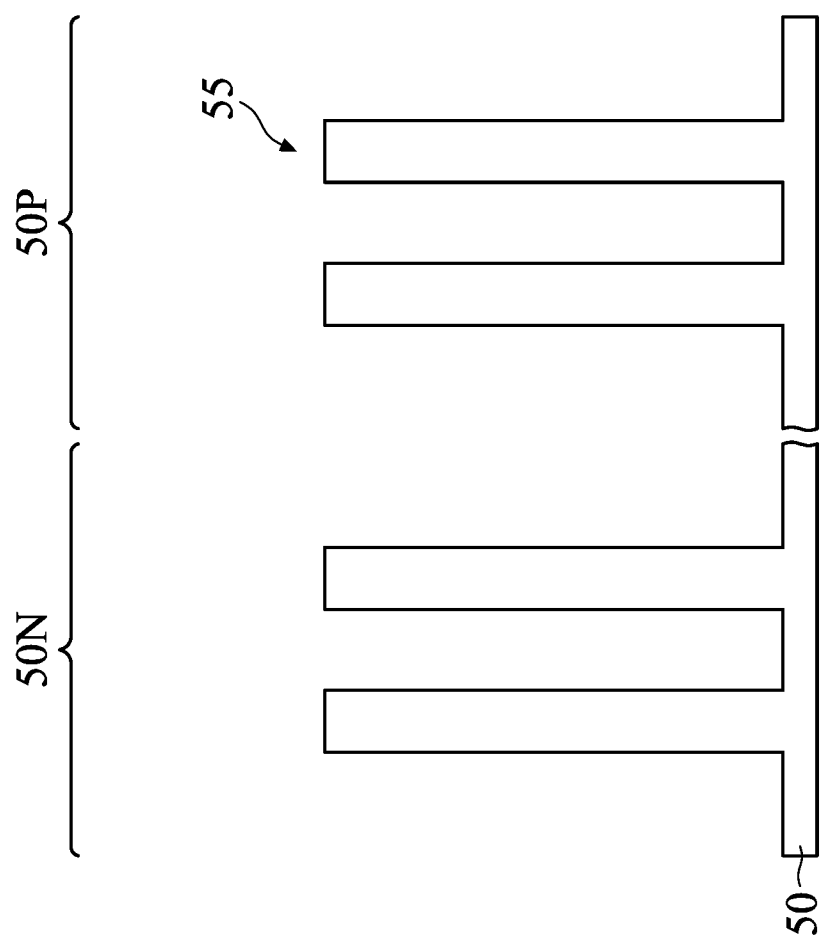

In FIG. 3, fins 55 are formed in the substrate 50. The fins 55 are semiconductor strips. In some embodiments, the fins 55 may be formed in the substrate 50 by etching trenches in the substrate 50. The etching may be any acceptable etch process, such as a reactive ion etch (RIE), a neutral beam etch (NBE), the like, or a combination thereof. The etch may be anisotropic.

The fins 55 may be patterned by any suitable method. For example, the fins 55 may be patterned using one or more photolithography processes, including double-patterning or multi-patterning processes. Generally, double-patterning or multi-patterning processes combine photolithography and self-aligned processes, allowing patterns to be created that have, for example, pitches smaller than what is otherwise obtainable using a single, direct photolithography process. For example, in some embodiments, a sacrificial layer is formed over a substrate and patterned using a photolithography process. Spacers are formed alongside the patterned sacrificial layer using a self-aligned process. The sacrificial layer is then removed, and the remaining spacers may then be used to pattern the fins 55. In some embodiments, the mask (or other layer) may remain on the fins 55.

Figure 4:
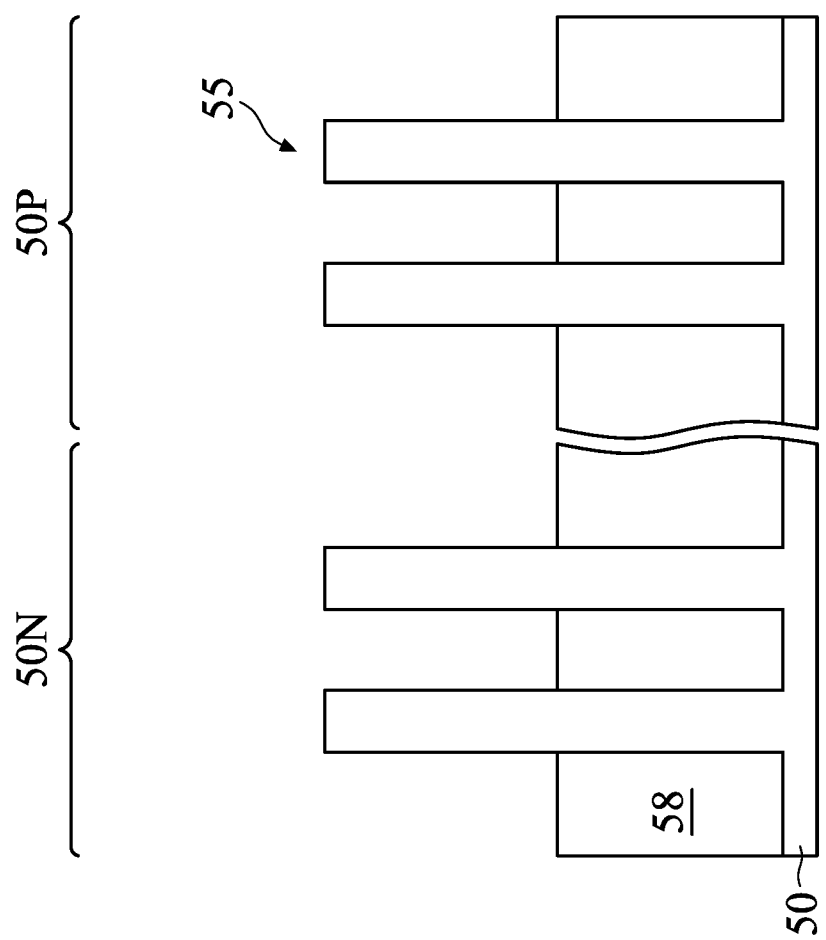

In FIG. 4, shallow trench isolation (STI) regions 58 are formed adjacent the fins 55. The STI regions 58 may be formed by forming an insulation material (not separately illustrated) over the substrate 50 and between neighboring fins 55. The insulation material may be an oxide, such as silicon oxide, a nitride, the like, or a combination thereof, and may be formed by a high density plasma chemical vapor deposition (HDP-CVD), a flowable CVD (FCVD) (e.g., a CVD-based material deposition in a remote plasma system with post curing to convert the deposited material to another material, such as an oxide), the like, or a combination thereof. Other insulation materials formed by any acceptable process may be used. In the illustrated embodiment, the insulation material is silicon oxide formed by an FCVD process. An anneal process may be performed once the insulation material is formed. In some embodiments, the insulation material is formed such that excess insulation material covers the fins 55. The insulation material may comprise a single layer or may utilize multiple layers. For example, in some embodiments a liner (not separately illustrated) may first be formed along surfaces of the substrate 50 and the fins 55. Thereafter, a fill material, such as those discussed above may be formed over the liner.

A removal process is then applied to the insulation material to remove excess insulation material over the fins 55. In some embodiments, a planarization process such as a chemical mechanical polish (CMP), an etch-back process, combinations thereof, or the like may be utilized. The planarization process may planarize the insulation material and the fins 55. The planarization process exposes the fins 55 such that top surfaces of the fins 55 and the insulation material are level after the planarization process is complete.

The insulation material is then recessed to form the STI regions 58 as illustrated in FIG. 4. The insulation material is recessed such that upper portions of the fins 55 and the substrate 50 protrude from between neighboring STI regions 58. Further, the top surfaces of the STI regions 58 may have flat surfaces as illustrated, convex surfaces, concave surfaces (such as dishing), or a combination thereof. The top surfaces of the STI regions 58 may be formed flat, convex, and/or concave by an appropriate etch. The STI regions 58 may be recessed using an acceptable etching process, such as one that is selective to the material of the insulation material (e.g., etches the material of the insulation material at a faster rate than the material of the fins 55 and the substrate 50). For example, an oxide removal using, for example, dilute hydrofluoric (dHF) acid may be used.

The process described with respect to FIGS. 2-4 is just one example of how the fins 55 may be formed. In some embodiments, the fins 55 may be formed by an epitaxial growth process. For example, a dielectric layer can be formed over a top surface of the substrate 50, and trenches can be etched through the dielectric layer to expose the underlying substrate 50. Homoepitaxial structures can be epitaxially grown in the trenches, and the dielectric layer can be recessed such that the homoepitaxial structures protrude from the dielectric layer to form fins. Additionally, in some embodiments, heteroepitaxial structures can be used for the fins 55. For example, the fins 55 in FIG. 4 can be recessed, and a material different from the fins 55 may be epitaxially grown over the recessed fins 55. In such embodiments, the fins 55 comprise the recessed material as well as the epitaxially grown material disposed over the recessed material. In some embodiments, a dielectric layer can be formed over a top surface of the substrate 50, and trenches can be etched through the dielectric layer. Heteroepitaxial structures can then be epitaxially grown in the trenches using a material different from the substrate 50, and the dielectric layer can be recessed such that the heteroepitaxial structures protrude from the dielectric layer to form the fins 55. In some embodiments where homoepitaxial or heteroepitaxial structures are epitaxially grown, the epitaxially grown materials may be in situ doped during growth, which may obviate prior and subsequent implantations although in situ and implantation doping may be used together.

Still further, it may be advantageous to epitaxially grow a material in region 50N (e.g., an NMOS region) different from the material in region 50P (e.g., a PMOS region). In some embodiments, upper portions of the fins 55 may be formed from silicon-germanium ($Si_xGe_{1-x}$, where x can be in the range of 0 to 1), silicon carbide, pure or substantially pure germanium, a III-V compound semiconductor, a II-VI compound semiconductor, or the like. For example, the available materials for forming III-V compound semiconductor include, but are not limited to, indium arsenide, aluminum arsenide, gallium arsenide, indium phosphide, gallium nitride, indium gallium arsenide, indium aluminum arsenide, gallium antimonide, aluminum antimonide, aluminum phosphide, gallium phosphide, and the like.

Further in FIG. 4, appropriate wells (not separately illustrated) may be formed in the fins 55 and/or the substrate 50. In some embodiments, a P well may be formed in the region 50N, and an N well may be formed in the region 50P. In some embodiments, a P well or an N well are formed in both the region 50N and the region 50P.

In the embodiments with different well types, the different implant steps for the region 50N and the region 50P may be achieved using a photoresist or other masks (not separately illustrated). For example, a photoresist may be formed over the fins 55 and the STI regions 58 in the region 50N. The photoresist is patterned to expose the region 50P of the substrate 50, such as a PMOS region. The photoresist can be formed by using a spin-on technique and can be patterned using acceptable photolithography techniques. Once the photoresist is patterned, an n-type impurity implant is performed in the region 50P, and the photoresist may act as a mask to substantially prevent n-type impurities from being implanted into the region 50N, such as an NMOS region. The n-type impurities may be phosphorus, arsenic, antimony, or the like implanted in the region to a concentration of equal to or less than $1\times10^{18}$ atoms/cm$^3$, such as between about $1\times10^{16}$ atoms/cm$^3$ and about $1\times10^{18}$ atoms/cm$^3$. After the implant, the photoresist is removed, such as by an acceptable ashing process.

Following the implanting of the region 50P, a photoresist is formed over the fins 55 and the STI regions 58 in the region 50P. The photoresist is patterned to expose the region 50N of the substrate 50, such as the NMOS region. The photoresist can be formed by using a spin-on technique and can be patterned using acceptable photolithography techniques. Once the photoresist is patterned, a p-type impurity implant may be performed in the region 50N, and the photoresist may act as a mask to substantially prevent p-type impurities from being implanted into the region 50P, such as the PMOS region. The p-type impurities may be boron, boron fluoride, indium, or the like implanted in the region to a concentration of equal to or less than $1\times10^{18}$ atoms/cm$^3$, such as between about $1\times10^{16}$ atoms/cm$^3$ and about $1\times10^{18}$ atoms/cm$^3$. After the implant, the photoresist may be removed, such as by an acceptable ashing process.

After the implants of the region 50N and the region 50P, an anneal may be performed to repair implant damage and to activate the p-type and/or n-type impurities that were implanted. In some embodiments, the grown materials of epitaxial fins may be in situ doped during growth, which may obviate the implantations, although in situ and implantation doping may be used together.

Figure 5:
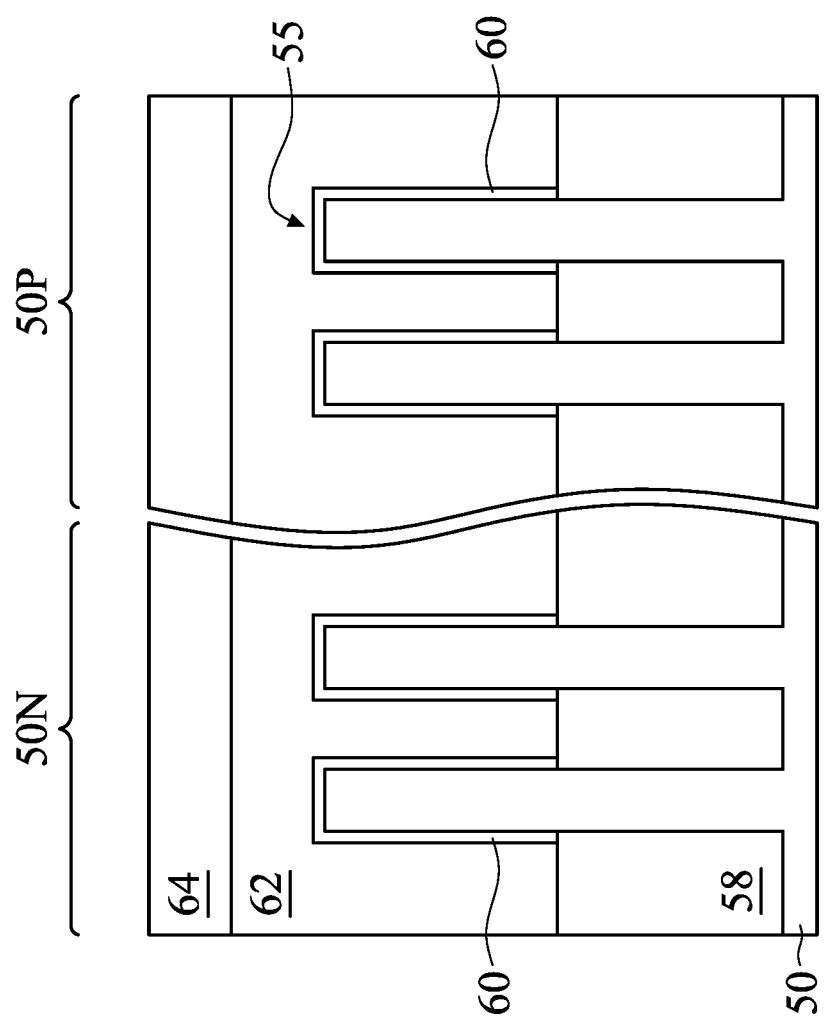

In FIG. 5, dummy dielectric layers 60 are formed on the fins 55 and the substrate 50. The dummy dielectric layers 60 may be, for example, silicon oxide, silicon nitride, a combination thereof, or the like, and may be deposited or thermally grown according to acceptable techniques. A dummy gate layer 62 is formed over the dummy dielectric layers 60, and a mask layer 64 is formed over the dummy gate layer 62. The dummy gate layer 62 may be deposited over the dummy dielectric layers 60 and then planarized by a process such as CMP. The mask layer 64 may be deposited over the dummy gate layer 62. The dummy gate layer 62 may be conductive or non-conductive materials and may be selected from a group including amorphous silicon, polycrystalline-silicon (polysilicon), polycrystalline silicon-germanium (poly-SiGe), metallic nitrides, metallic silicides, metallic oxides, and metals. The dummy gate layer 62 may be deposited by physical vapor deposition (PVD), CVD, sputter deposition, or other techniques known and used in the art for depositing the selected material. The dummy gate layer 62 may be made of other materials that have a high etching selectivity from the material of the STI regions 58. The mask layer 64 may include, for example, silicon nitride, silicon oxynitride, or the like. In this example, a single dummy gate layer 62 and a single mask layer 64 are formed across the region 50N and the region 50P. It is noted that the dummy dielectric layers 60 are shown covering only the fins 55 and the substrate 50 for illustrative purposes only. In some embodiments, the dummy dielectric layers 60 may be deposited such that the dummy dielectric layers 60 cover the STI regions 58, extending between the dummy gate layer 62 and the STI regions 58.

FIGS. 6A through 17D illustrate various additional steps in the manufacturing of embodiment devices. FIGS. 6A through 17D illustrate features in either of the region 50N or the region 50P. For example, the structures illustrated in FIGS. 6A through 17D may be applicable to both the region 50N and the region 50P. Differences (if any) in the structures of the region 50N and the region 50P are described in the text accompanying each figure.

Figure 6B:
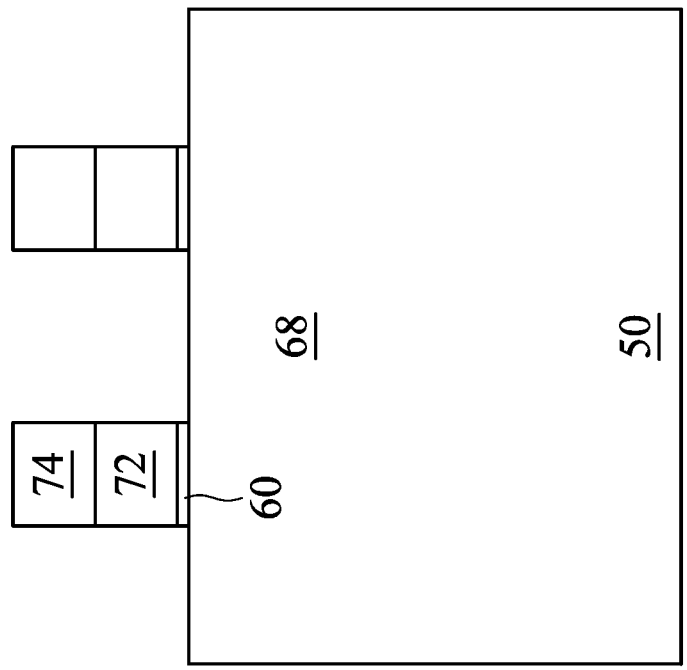
Figure 6A:
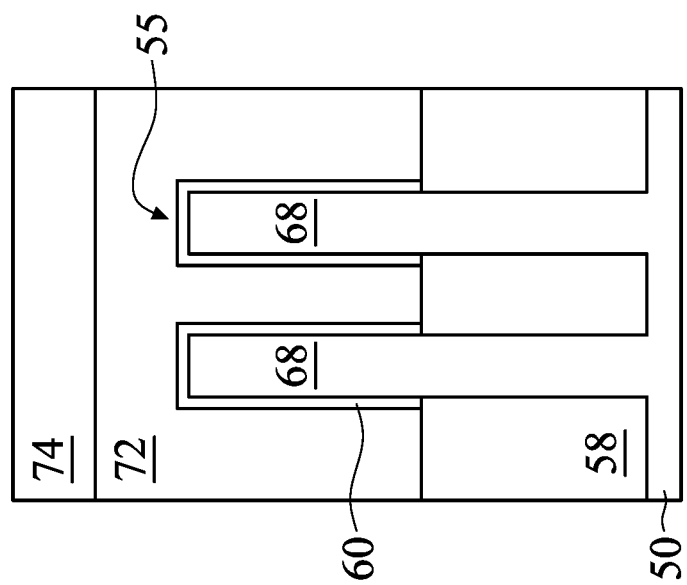

In FIGS. 6A and 6B, the mask layer 64 (see FIG. 5) may be patterned using acceptable photolithography and etching techniques to form masks 74. An acceptable etching technique may be used to transfer the pattern of the masks 74 to the dummy gate layer 62 to form dummy gates 72. In some embodiments, the pattern of the masks 74 may also be transferred to the dummy dielectric layers 60. The dummy gates 72 cover respective channel regions 68 of the fins 55. The pattern of the masks 74 may be used to physically separate each of the dummy gates 72 from adjacent dummy gates. The dummy gates 72 may also have a lengthwise direction substantially perpendicular to the lengthwise direction of respective epitaxial fins 55. The dummy dielectric layers 60, the dummy gates 72, and the masks 74 may be collectively referred to as "dummy gate stacks."

Figure 7B:
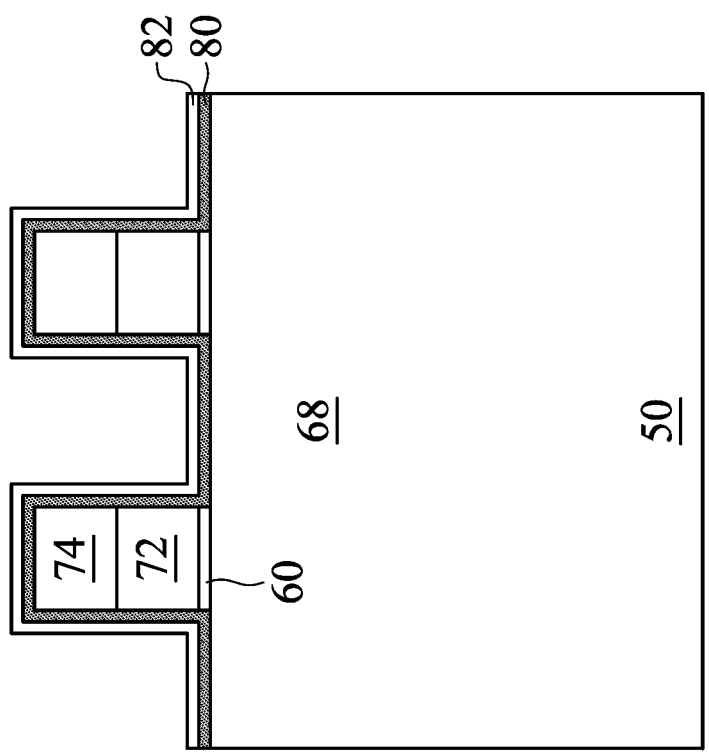
Figure 7A:
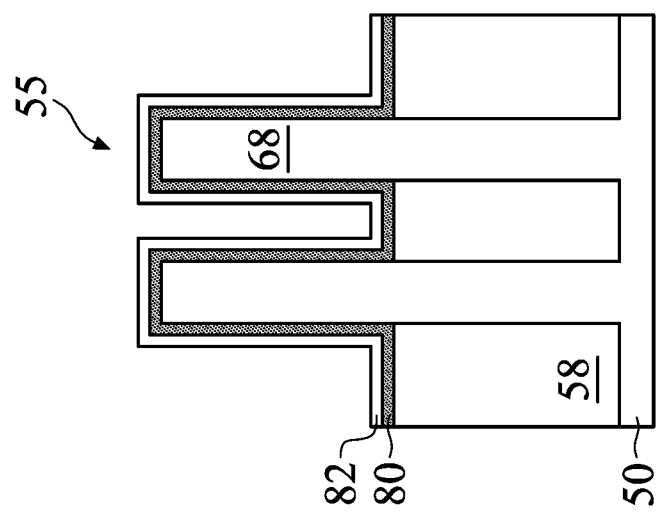

In FIGS. 7A and 7B, a first spacer layer 80 and a second spacer layer 82 are formed over the structures illustrated in FIGS. 6A and 6B. In FIGS. 7A and 7B, the first spacer layer 80 is formed on top surfaces of the STI regions 58, top surfaces and sidewalls of the fins 55 and the masks 74, and sidewalls of the dummy gates 72 and the dummy dielectric layers 60. The second spacer layer 82 is deposited over the first spacer layer 80. The first spacer layer 80 may be formed by thermal oxidation or deposited by CVD, ALD, or the like. The first spacer layer 80 may be formed of silicon oxide, silicon nitride, silicon oxynitride, or the like. The second spacer layer 82 may be deposited by CVD, ALD, or the like. The second spacer layer 82 may be formed of silicon oxide, silicon nitride, silicon oxynitride, or the like.

Figure 8B:
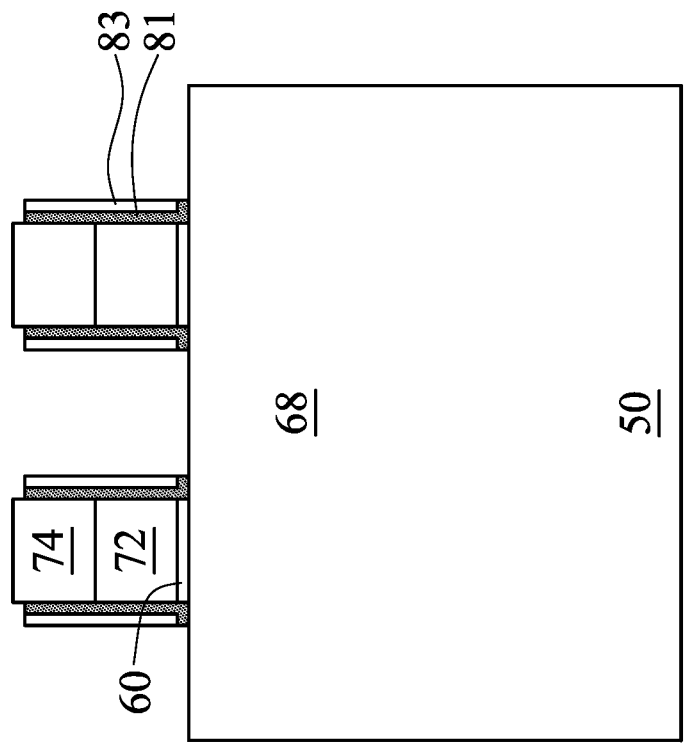
Figure 8A:
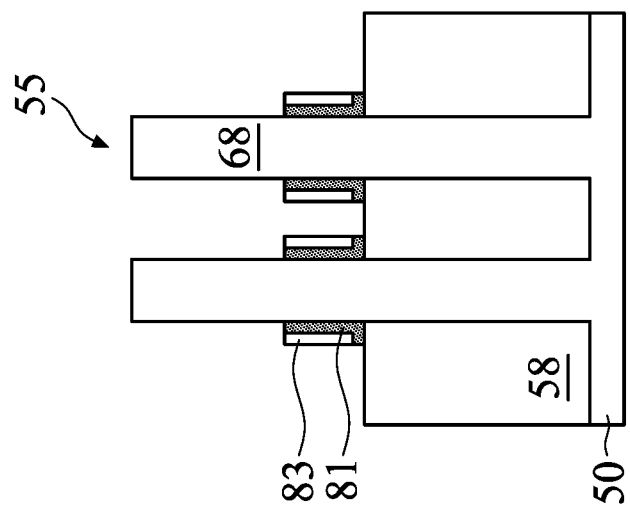

In FIGS. 8A and 8B, the first spacer layer 80 and the second spacer layer 82 are etched to form first spacers 81 and second spacers 83. The first spacer layer 80 and the second spacer layer 82 may be etched using a suitable etching process, such as an anisotropic etching process (e.g., a dry etching process) or the like. The first spacers 81 and the second spacers 83 may be disposed on sidewalls of the fins 55, the dummy dielectric layers 60, the dummy gates 72, and the masks 74. The first spacers 81 and the second spacers 83 may have different heights adjacent the fins 55 and the dummy gate stacks due to the etching processes used to etch the first spacer layer 80 and the second spacer layer 82, as well as differing heights between the fins 55 and the dummy gate stacks. Specifically, as illustrated in FIGS. 8A and 8B, in some embodiments, the first spacers 81 and the second spacers 83 may extend partially up sidewalls of the fins 55 and the dummy gate stacks. In some embodiments, the first spacers 81 and the second spacers 83 may extend to top surfaces of the dummy gate stacks.

After the first spacers 81 and the second spacers 83 are formed, implants for lightly doped source/drain (LDD) regions (not separately illustrated) may be performed. In embodiments with different device types, similar to the implants discussed above in FIG. 4, a mask, such as a photoresist, may be formed over the region 50N, while exposing the region 50P, and appropriate type (e.g., p-type) impurities may be implanted into the exposed fins 55 and the substrate 50 in the region 50P. The mask may then be removed. Subsequently, a mask, such as a photoresist, may be formed over the region 50P while exposing the region 50N, and appropriate type impurities (e.g., n-type) may be implanted into the exposed fins 55 and the substrate 50 in the region 50N. The mask may then be removed. The n-type impurities may be the any of the n-type impurities previously discussed, and the p-type impurities may be the any of the p-type impurities previously discussed. The lightly doped source/drain regions may have a concentration of impurities of from about $1 \times 10^{15}$ atoms/cm$^3$ to about $1 \times 10^{19}$ atoms/cm$^3$. An anneal may be used to repair implant damage and to activate the implanted impurities.

It is noted that the above disclosure generally describes a process of forming spacers and LDD regions. Other processes and sequences may be used. For example, fewer or additional spacers may be utilized, different sequence of steps may be utilized (e.g., the first spacers 81 may be formed prior to forming the second spacers 83, additional spacers may be formed and removed, and/or the like). Furthermore, the n-type and p-type devices may be formed using a different structures and steps.

Figure 9B:
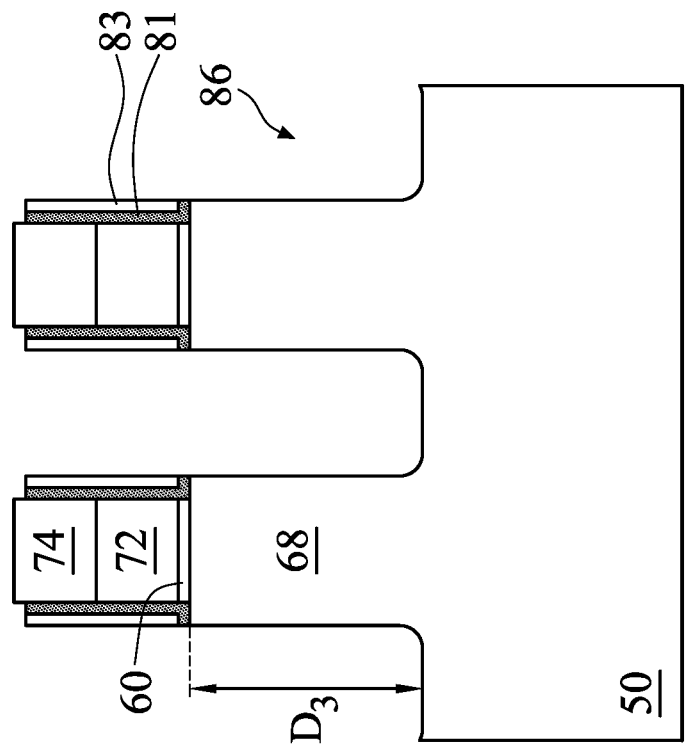
Figure 9A:
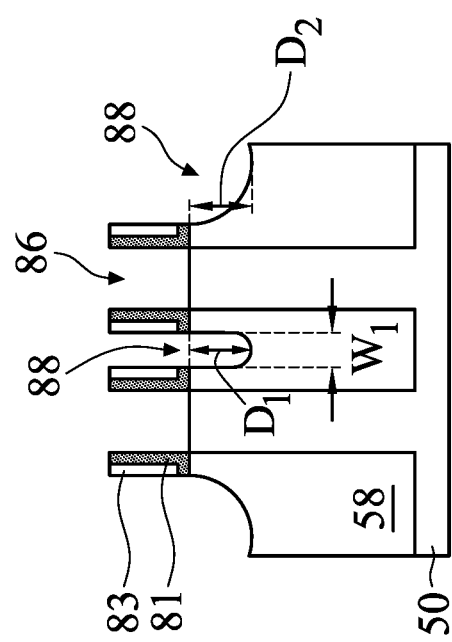

In FIGS. 9A-9C, first recesses 86 are formed in the fins 55 and the substrate 50 and second recesses 88 are formed in the STI regions 58. As illustrated in FIG. 9A, top surfaces of the STI regions 58 may be level with top surfaces of the substrate 50. The substrate 50 may be etched such that bottom surfaces of the first recesses 86 are disposed above or below the top surfaces of the STI regions 58. The fins 55 may be etched to form the first recesses 86 such that epitaxial source/drain regions (such as the epitaxial source/drain regions 92, discussed below with respect to FIGS. 11A-11C) can be subsequently formed in the first recesses 86. The etching processes used to form the first recesses 86 may be selective to the material of the fins 55 and the substrate 50 (e.g., etching processes that etch the material of the fins 55 and the substrate 50 at a faster rate than the material of the STI regions 58). However, some material from the STI regions 58 may be removed by the etching processes used to form the first recesses 86, forming the second recesses 88.

The first recesses 86 and the second recesses 88 may be formed by etching the fins 55, the substrate 50, and the STI regions 58 using anisotropic etching processes, such as RIE, NBE, or the like. In some embodiments, process gases used in etching the fins 55, the substrate 50, and the STI regions 58 may include hydrogen bromide (HBr), methane (CH$_4$), and helium (He), although any suitable process gases may be used to etch the fins 55, the substrate 50, and the STI regions 58. The first spacers 81, the second spacers 83, and the masks 74 mask portions of the fins 55, the substrate 50, and the STI regions 58 during the etching processes used to form the first recesses 86 and the second recesses 88. A single etch process or multiple etch processes may be used to form the first recesses 86 and the second recesses 88. Timed etch processes may be used to stop the etching of the first recesses 86 and the second recesses 88 after the first recesses 86 reach a desired depth.

As illustrated in FIG. 9A, the second recesses 88 formed between adjacent fins 55 may have widths W$_1$ from about 3 nm to about 5 nm or from about 3 nm to about 10 nm and depths D$_1$ from about 3 nm to about 8 nm or from about 3 nm to about 20 nm. The second recesses 88 disposed outside of adjacent fins 55 may have depths D$_2$ from about 5 nm to about 25 nm or from about 10 nm to about 20 nm. As illustrated in FIG. 9B, the first recesses 86 formed in the fins 55 and the substrate 50 may have a depth D$_3$ from about 40 nm to about 60 nm or from about 45 nm to about 55 nm. As illustrated in FIG. 9C, the second recesses formed adjacent the dummy gate stacks may have widths W$_2$ from about 20 nm to about 28 nm or from about 22 nm to about 26 nm and depths D$_4$ from about 5 nm to about 25 nm or from about 10 nm to about 20 nm.

Figure 10B:
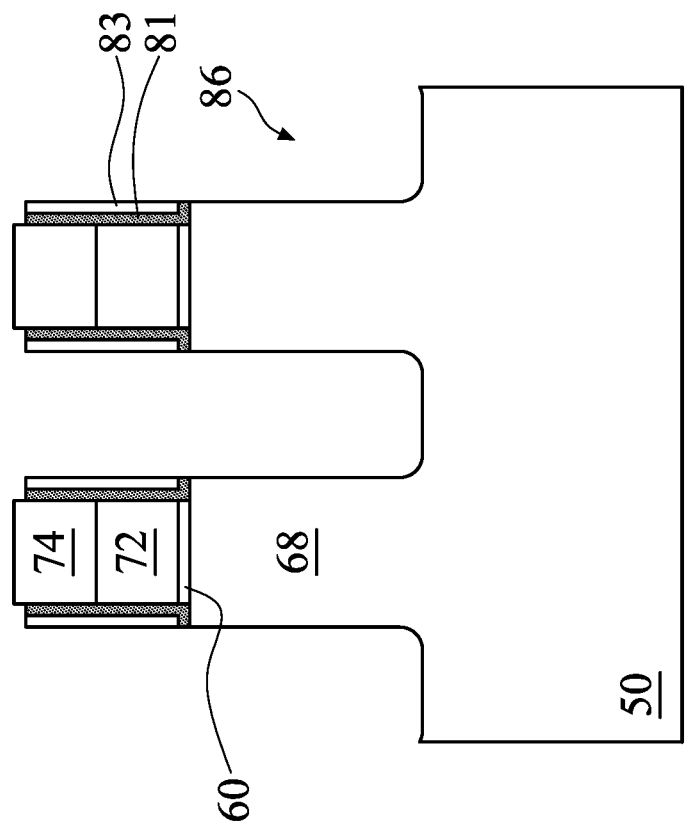
Figure 10A:
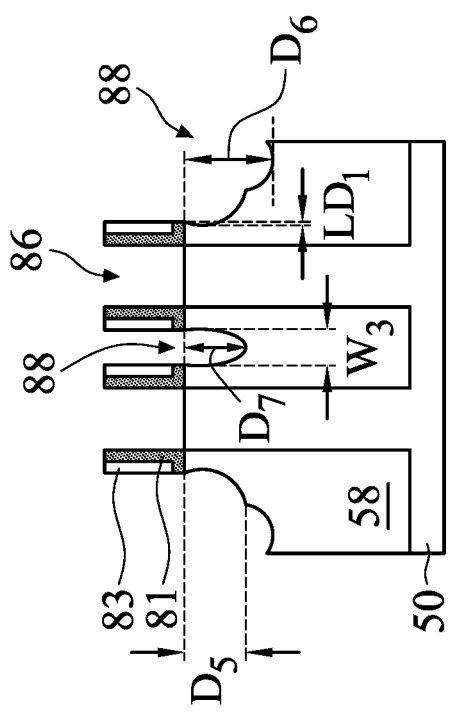
Figure 10C:
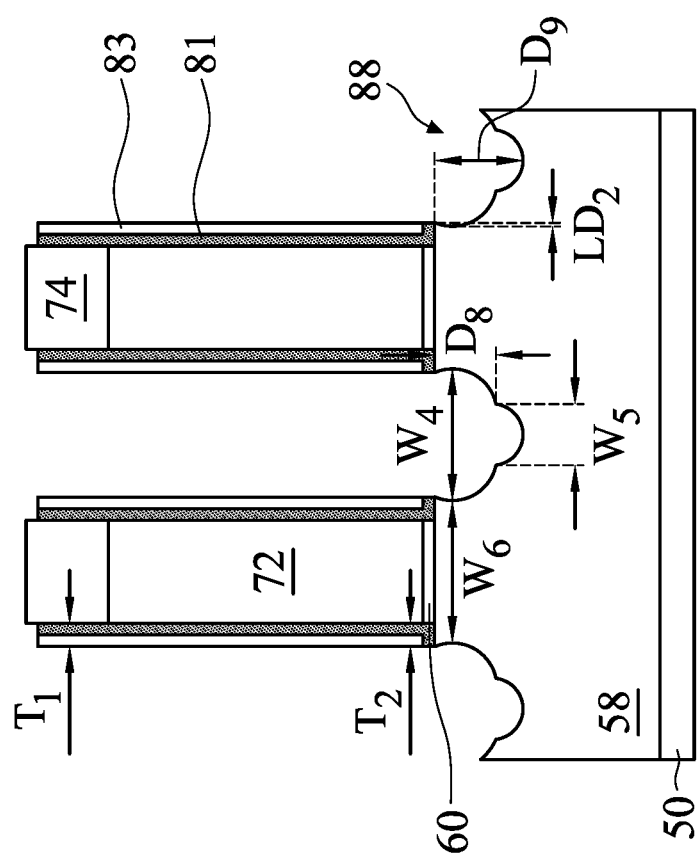

In FIGS. 10A-10C, a pre-clean process is performed to remove an oxide (e.g., a native oxide) from surfaces of the fins 55 and the substrate 50 adjacent the first recesses 86. The pre-clean process may also remove material from the STI regions 58, extending the second recesses 88. The pre-clean process may be performed by an isotropic dry etching process or the like. In some embodiments, the pre-clean process may use a plasma-less gaseous etching process. The pre-clean process may use a first process gas, such as hydrogen fluoride (HF), and a second process gas, such as ammonia (NH$_3$), argon (Ar), helium (He), hydrogen (H$_2$), a combination thereof, or the like. A flowrate of the first process gas during the pre-clean process may be from about 2 sccm to about 7 sccm or from about 3 sccm to about 5 sccm and a flowrate of the second process gas may be from about 6 sccm to about 20 sccm or from about 10 sccm to about 16 sccm. A ratio of the flowrate of the first process gas to the second process gas may be from about 1:10 to about 1:1 or from about 1:5 to about 1:2. The pre-clean process may be performed at a temperature from about 5° C. to about 15° C., at a pressure from about 1 Torr to about 3 Torr, and for a time period ranging from about 70 seconds to about 80 seconds. The pre-clean process may remove an oxide layer having a thickness of less than about 4 nm or from about 3 nm to about 5 nm from surfaces of the fins 55 and the substrate 50 adjacent the first recesses 86.

Conventional pre-clean processes may use plasma-based dry etching processes which include radicals, such as fluorine (F) radicals. In comparison with the plasma-less gaseous cleaning process, conventional pre-clean processes may be performed at higher temperatures and higher pressures for shorter periods of time. In contrast to conventional pre-clean processes, which may use plasma-based processes or wet etching processes, using the plasma-less gaseous cleaning process reduces under-cutting of the STI regions 58 below the first spacers 81 and the second spacers 83. This increases breakdown voltage and results in devices having better performance and reduced device defects.

As illustrated in FIG. 10A, the second recesses 88 outside of the fins 55 may have a profile which has a first rounded profile extending to a depth $D_5$ from about 5 nm to about 25 nm or from about 10 nm to about 20 nm and a second rounded profile extending from the bottom of the first rounded profile to a depth $D_6$ from about 10 nm to about 30 nm or from about 15 nm to about 25 nm. A ratio of the depth $D_5$ to the depth $D_6$ may be from about 5:6 to about 2:3 or from about 4:5 to about 7:10. The second recesses 88 may undercut the first spacers 81 and the second spacers 83 by a lateral distance $LD_1$ of less than about 3 nm or from about 3 nm to about 5 nm. The second recesses 88 between adjacent fins 55 may have maximum widths $W_3$ from about 3 nm to about 5 nm, from about 5 nm to about 7 nm, or from about 5 nm to about 12 nm and depths $D_7$ from about 5 nm to about 10 nm or from about 5 nm to about 22 nm.

As illustrated in FIG. 10C, the second recesses 88 adjacent the dummy gate stacks may also have a profile which has a first rounded profile extending to a depth $D_8$ from about 5 nm to about 25 nm, from about 7 nm to about 27 nm, or from about 10 nm to about 20 nm and a second rounded profile extending from the bottom of the first rounded profile to a depth $D_9$ from about 10 nm to about 30 nm or from about 15 nm to about 25 nm. A ratio of the depth $D_8$ to the depth $D_9$ may be from about 5:6 to about 2:3 or from about 4:5 to about 7:10. The second recesses 88 may undercut the first spacers 81 and the second spacers 83 by a lateral distance $LD_2$ of less than about 3 nm or from about 3 nm to about 5 nm. The first rounded profile may have a maximum width $W_4$ from about 25 nm to about 30 nm or from about 26 nm to about 29 nm and the second rounded profile may have a maximum width $W_5$ from about 5 nm to about 10 nm or from about 6 nm to about 9 nm. A ratio of the width $W_4$ to the width $W_5$ may be from about 6:1 to about 5:1. A width $W_6$ of the STI regions 58 separating adjacent second recesses 88 may be greater than about 24 nm or from about 20 nm to about 28 nm. Following the formation of the first recesses 86 and the second recesses 88, the first spacers 81 and the second spacers 83 may have a thickness $T_1$ adjacent a top of the dummy gate stacks and a thickness $T_2$ adjacent a bottom of the dummy gate stacks. A ratio of the thickness $T_2$ to the thickness $T_1$ may be from about 1 to about 1.2 or from about 1.05 to about 1.15.

Performing the pre-clean process using the first process gas and the second process gas allows for the oxide layer to be removed from surfaces of the fins 55 and the substrate 50 adjacent the first recesses 86, while minimizing the amount of material removed from the STI regions 58. In some embodiments, the pre-clean process may have less lateral etching than other methods of removing the oxide layer, and may produce STI regions 58 and second recesses 88 having a better profile. For example, less of a kink may be formed adjacent interfaces of the dummy gate stacks and the top of the STI regions 58. Using the pre-clean process results in devices formed by methods including the pre-clean process having increased breakdown voltage, better performance, and reduced device defects.

After the pre-clean process is performed, implants may be performed on the STI regions 58. The implants may be used to increase the resistance of the STI regions 58, which may further increase breakdown voltage, improve performance, and reduce device defects. Impurities such as phosphorous ions, boron ions, combinations thereof, or the like may be implanted into the STI regions 58. The STI regions 58 may have a concentration of impurities of greater than about $1\times10^{15}$ atoms/cm$^3$ or from about $1\times10^{15}$ atoms/cm$^3$ to about $1\times10^{16}$ atoms/cm$^3$. The impurities may be implanted at a temperature from about 50° C. to about 70° C. or from about 55° C. to about 65° C. An anneal may be used to repair implant damage and to activate the implanted impurities.

Figure 11B:
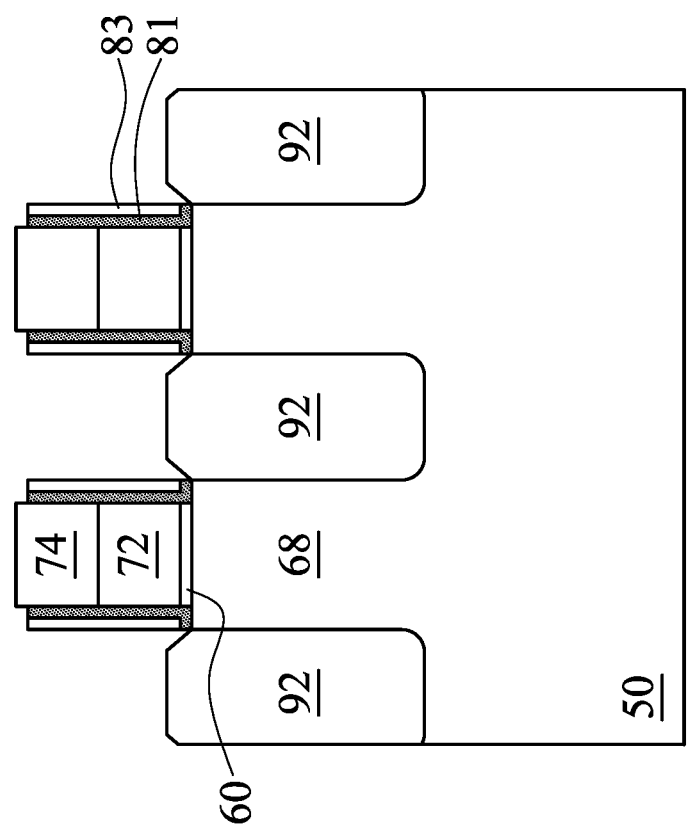
Figure 11A:
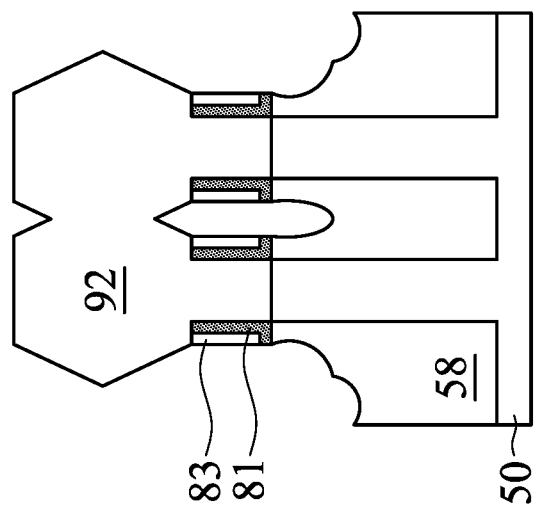
Figure 11C:
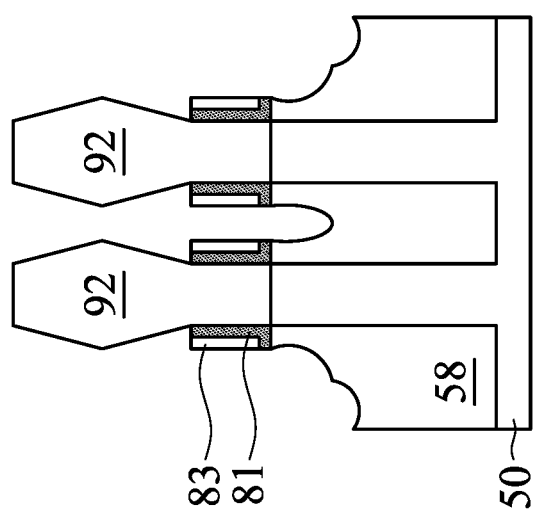
Figure 12B:
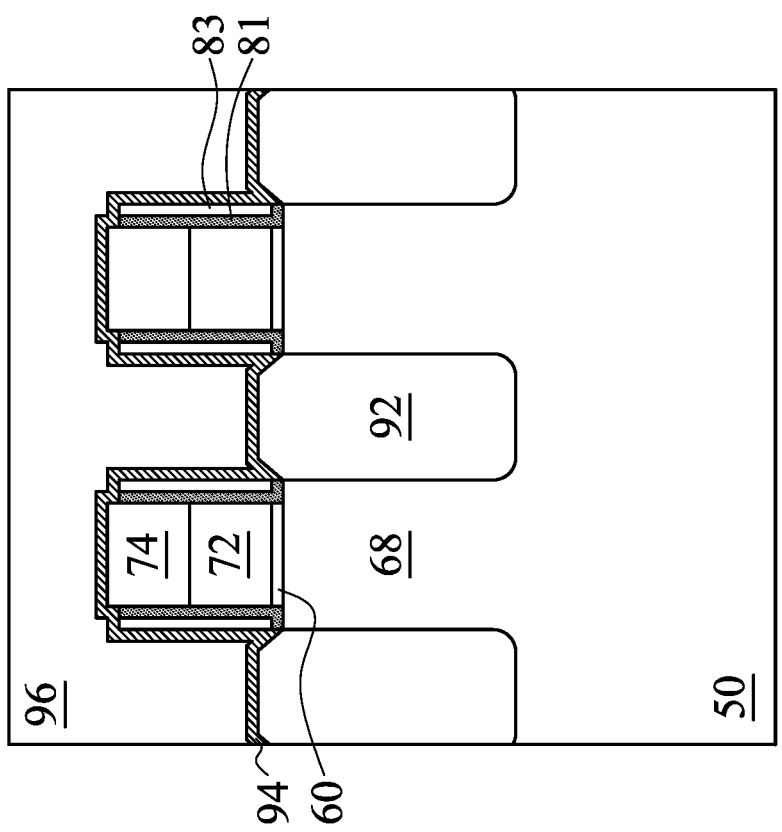
Figure 12A:
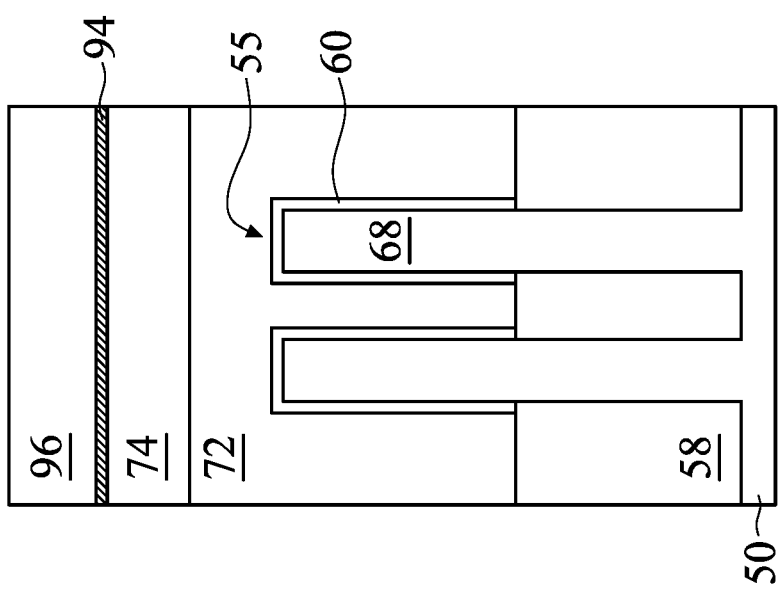
Figure 12D:
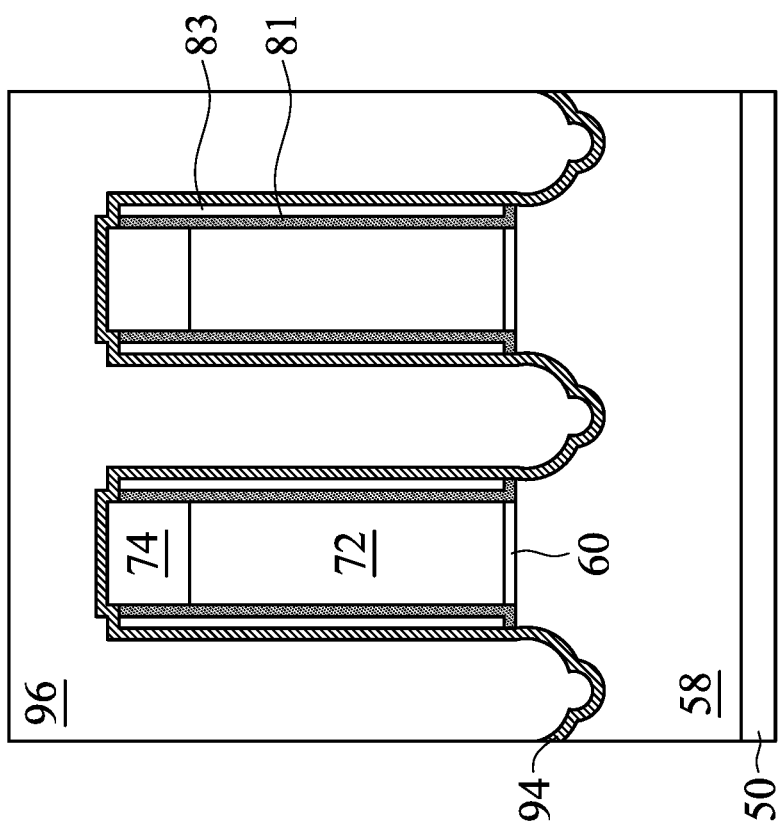
Figure 12C:
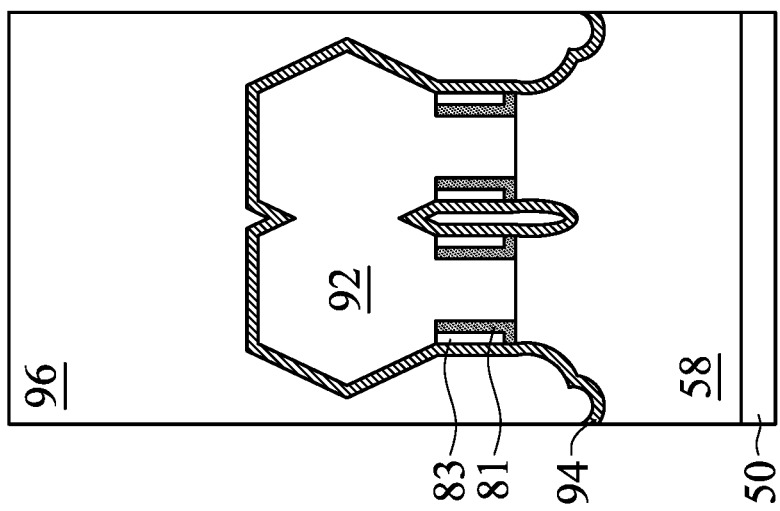

In FIGS. 11A-11C, epitaxial source/drain regions 92 are formed in the first recesses 86 to exert stress on the channel regions 68 of the fins 55, thereby improving performance. As illustrated in FIG. 10B, the epitaxial source/drain regions 92 are formed in the first recesses 86 such that each dummy gate 72 is disposed between respective neighboring pairs of the epitaxial source/drain regions 92. In some embodiments, the first spacers 81 are used to separate the epitaxial source/drain regions 92 from the dummy gates 72 by an appropriate lateral distance so that the epitaxial source/drain regions 92 do not short out subsequently formed gates of the resulting FinFETs.

The epitaxial source/drain regions 92 in the region 50N, e.g., the NMOS region, may be formed by masking the region 50P, e.g., the PMOS region. Then, the epitaxial source/drain regions 92 are epitaxially grown in the first recesses 86. The epitaxial source/drain regions 92 may include any acceptable material, such as appropriate for n-type FinFETs. For example, if the fins 55 are silicon, the epitaxial source/drain regions 92 may include materials exerting a tensile strain on the fins 55, such as silicon, silicon carbide, phosphorous doped silicon carbide, silicon phosphide, or the like. The epitaxial source/drain regions 92 may have surfaces raised from respective surfaces of the fins 55 and may have facets.

The epitaxial source/drain regions 92 in the region 50P, e.g., the PMOS region, may be formed by masking the region 50N, e.g., the NMOS region. Then, the epitaxial source/drain regions 92 are epitaxially grown in the first recesses 86. The epitaxial source/drain regions 92 may include any acceptable material, such as appropriate for p-type NSFETs. For example, if the fins 55 are silicon, the epitaxial source/drain regions 92 may comprise materials exerting a compressive strain on the fins 55, such as silicon-germanium, boron doped silicon-germanium, germanium, germanium tin, or the like. The epitaxial source/drain regions 92 may also have surfaces raised from respective surfaces of the fins 55 and may have facets.

The epitaxial source/drain regions 92, the fins 55, and/or the substrate 50 may be implanted with dopants to form source/drain regions, similar to the process previously discussed for forming lightly-doped source/drain regions, followed by an anneal. The source/drain regions may have an impurity concentration of between about $1\times10^{19}$ atoms/cm$^3$ and about $1\times10^{21}$ atoms/cm$^3$. The n-type and/or p-type impurities for source/drain regions may be any of the impurities previously discussed. In some embodiments, the epitaxial source/drain regions 92 may be in situ doped during growth.

As a result of the epitaxy processes used to form the epitaxial source/drain regions 92 in the region 50N and the region 50P, upper surfaces of the epitaxial source/drain regions 92 have facets which expand laterally outward beyond sidewalls of the fins 55. In some embodiments, these facets cause adjacent epitaxial source/drain regions 92 of a same FinFET to merge as illustrated by FIG. 11A. In some embodiments, adjacent epitaxial source/drain regions 92 remain separated after the epitaxy process is completed as illustrated by FIG. 11C. In the embodiments illustrated in FIGS. 11A and 11C, the first spacers 81 may be formed covering portions of the sidewalls of the fins 55 that extend above the STI regions 58 thereby blocking the epitaxial growth. In some embodiments, the spacer etch used to form the first spacers 81 may be adjusted to remove the spacer material to allow the epitaxially grown region to extend to the surface of the STI region.

In FIGS. 12A-12D, a first interlayer dielectric (ILD) 96 is deposited over the structures illustrated in FIGS. 6A, 11A, 11B, and 10C (the processes of FIGS. 7A-10C do not alter the cross-section illustrated in FIGS. 6A, which illustrates the dummy gates 72 and the fins 55 protected by the dummy gates 72, and the processes of FIGS. 11A-11C do not alter the cross-section illustrated in FIG. 10C, which illustrates the second recesses 88 formed in the STI regions 58), respectively. The first ILD 96 may be formed of a dielectric material, and may be deposited by any suitable method, such as CVD, plasma-enhanced CVD (PECVD), or FCVD. Dielectric materials may include phospho-silicate glass (PSG), boro-silicate glass (BSG), boron-doped phospho-silicate glass (BPSG), undoped silicate glass (USG), or the like. Other insulation materials formed by any acceptable process may be used. In some embodiments, a contact etch stop layer (CESL) 94 is disposed between the first ILD 96 and the epitaxial source/drain regions 92, the masks 74, the first spacers 81, the second spacers 83, and the STI regions 58. The CESL 94 may comprise a dielectric material, such as, silicon nitride, silicon oxide, silicon oxynitride, or the like, having a different etch rate than the material of the overlying first ILD 96.

Figure 13B:
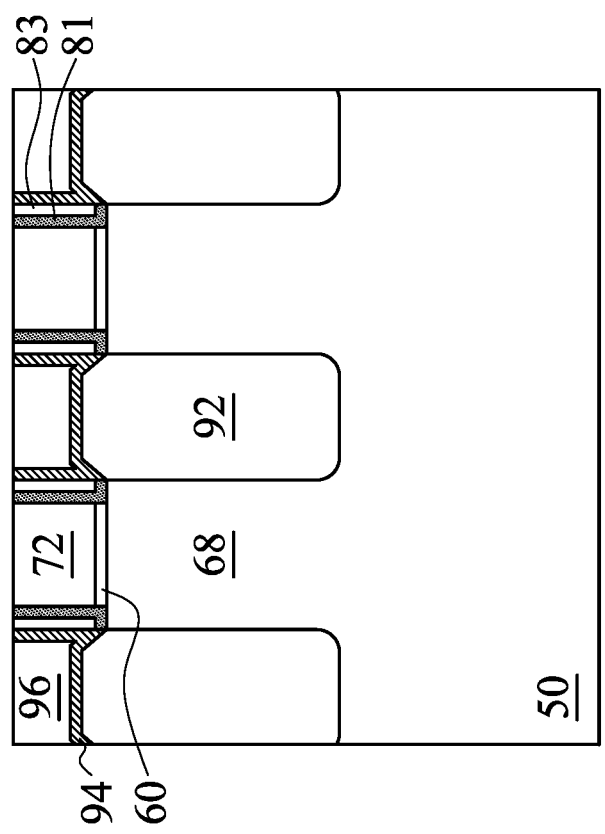
Figure 13A:
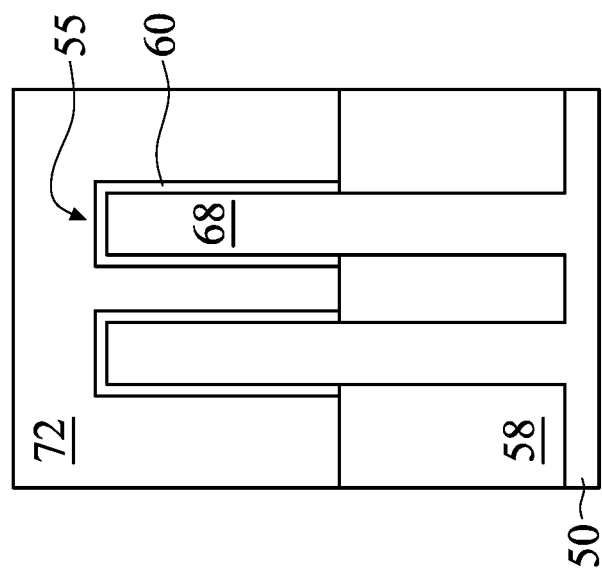

In FIGS. 13A and 13B, a planarization process, such as a CMP, may be performed to level the top surface of the first ILD 96 with the top surfaces of the dummy gates 72 or the masks 74. The planarization process may also remove the masks 74 on the dummy gates 72, and portions of the first spacers 81 along sidewalls of the masks 74. After the planarization process, top surfaces of the dummy gates 72, the first spacers 81, and the first ILD 96 are level. Accordingly, the top surfaces of the dummy gates 72 are exposed through the first ILD 96. In some embodiments, the masks 74 may remain, in which case the planarization process levels the top surface of the first ILD 96 with top surface of the masks 74 and the first spacers 81.

Figure 14B:
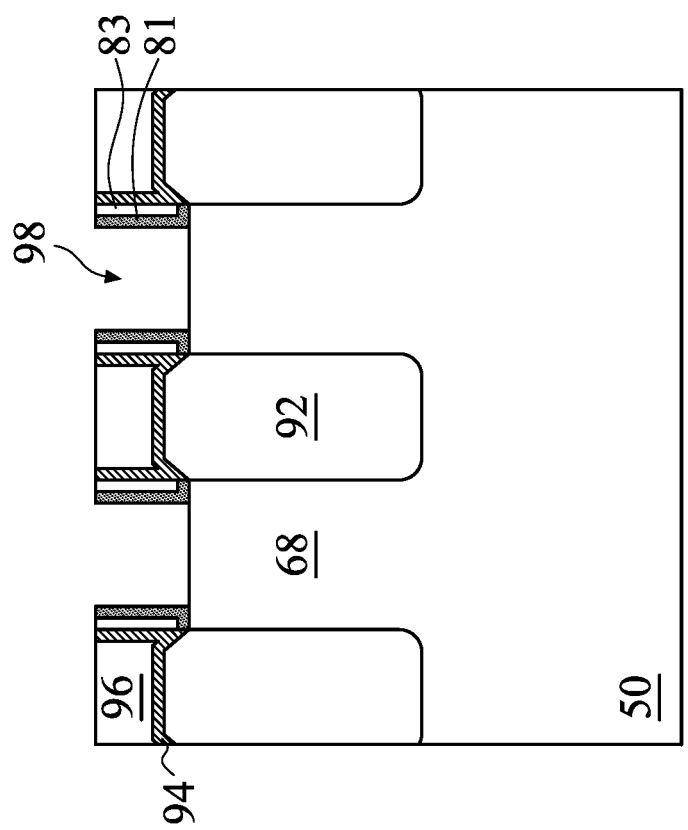
Figure 14A:
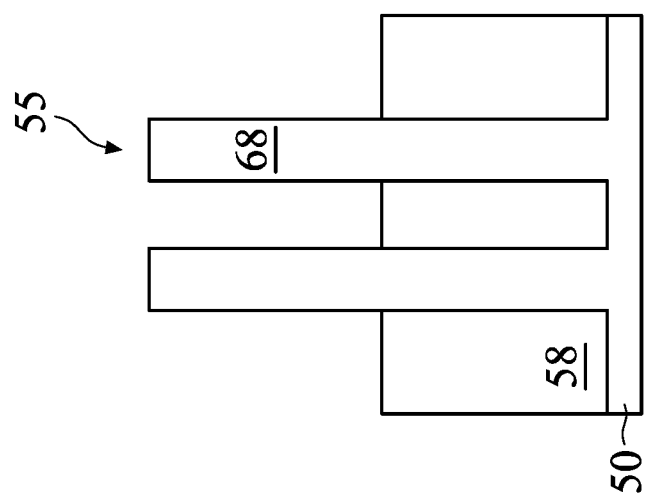

In FIGS. 14A and 14B, the dummy gates 72, and the masks 74 if present, are removed in an etching step(s), so that second recesses 98 are formed. Portions of the dummy dielectric layers 60 in the second recesses 98 may also be removed. In some embodiments, only the dummy gates 72 are removed and the dummy dielectric layers 60 remain and are exposed by the second recesses 98. In some embodiments, the dummy dielectric layers 60 are removed from second recesses 98 in a first region of a die (e.g., a core logic region) and remain in second recesses 98 in a second region of the die (e.g., an input/output region). In some embodiments, the dummy gates 72 are removed by an anisotropic dry etch process. For example, the etching process may include a dry etch process using reaction gas(es) that selectively etch the dummy gates 72 at a faster rate than the first ILD 96 or the first spacers 81. Each second recess 98 exposes and/or overlies a channel region 68 of a respective fin 55. Each channel region 68 is disposed between neighboring pairs of the epitaxial source/drain regions 92. During the removal, the dummy dielectric layer 60 may be used as an etch stop layer when the dummy gates 72 are etched. The dummy dielectric layer 60 may then be optionally removed after the removal of the dummy gates 72.

Figure 15B:
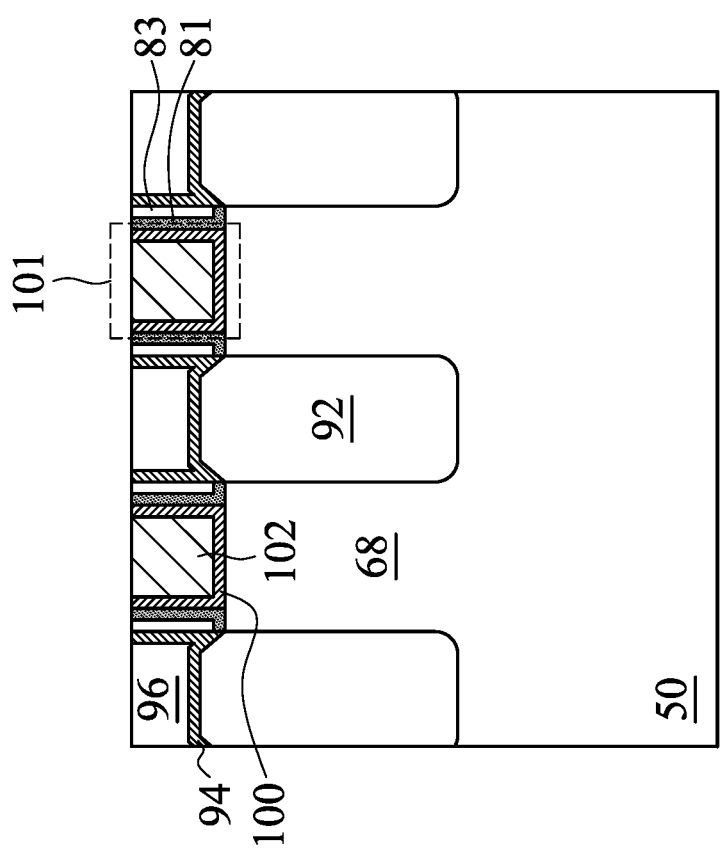
Figure 15A:
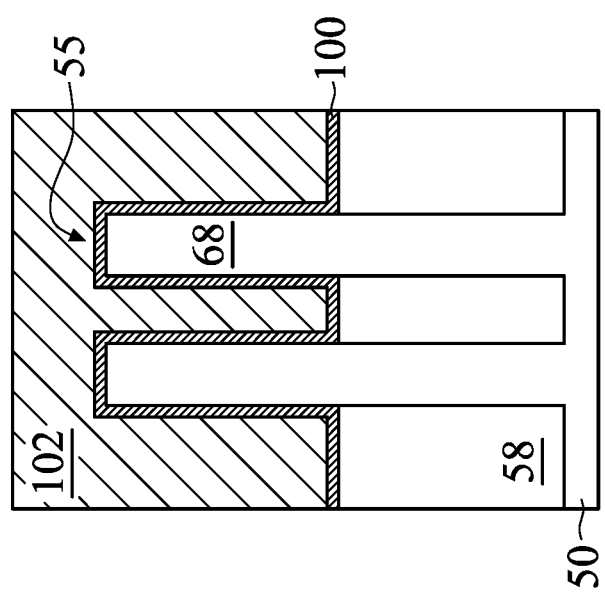
Figure 15C:
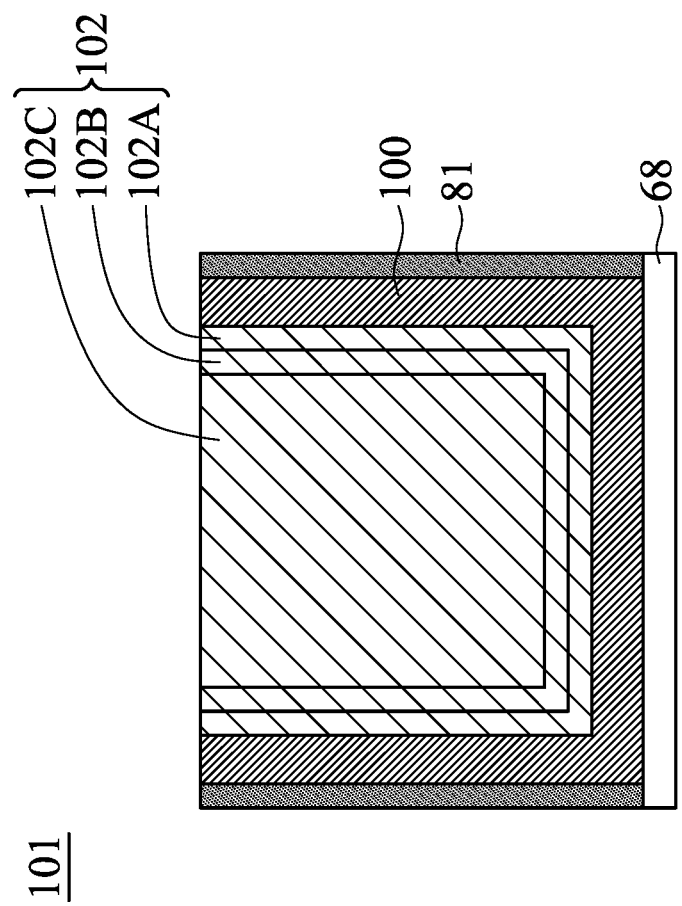

In FIGS. 15A and 15B, gate dielectric layers 100 and gate electrodes 102 are formed for replacement gates. FIG. 15C illustrates a detailed view of region 101 of FIG. 15B. The gate dielectric layers 100 are deposited conformally in the second recesses 98, such as on top surfaces and sidewalls of the fins 55 and the first spacers 81 and on top surfaces of the STI regions 58, the first ILD 96, the second spacers 83, and the CESL 94. In accordance with some embodiments, the gate dielectric layers 100 comprise silicon oxide, silicon nitride, or multilayers thereof. In some embodiments, the gate dielectric layers 100 include a high-k dielectric material, and in these embodiments, the gate dielectric layers 100 may have a k value greater than about 7.0, and may include a metal oxide or a silicate of hafnium, aluminum, zirconium, lanthanum, manganese, barium, titanium, lead, and combinations thereof. The formation methods of the gate dielectric layers 100 may include molecular-beam deposition (MBD), ALD, PECVD, or the like. In embodiments where portions of the dummy dielectric layers 60 remain in the second recesses 98, the gate dielectric layers 100 include a material of the dummy dielectric layers 60 (e.g., $SiO_2$).

The gate electrodes 102 are deposited over the gate dielectric layers 100, respectively, and fill the remaining portions of the second recesses 98. The gate electrodes 102 may include a metal-containing material such as titanium nitride, titanium oxide, tantalum nitride, tantalum carbide, cobalt, ruthenium, aluminum, tungsten, combinations thereof, or multi-layers thereof. For example, although a single layer gate electrode 102 is illustrated in FIG. 15B, the gate electrode 102 may comprise any number of liner layers 102A, any number of work function tuning layers 102B, and a fill material 102C as illustrated by FIG. 15C. After the filling of the second recesses 98, a planarization process, such as a CMP, may be performed to remove the excess portions of the gate dielectric layers 100 and the material of the gate electrodes 102, which excess portions are over the top surface of the first ILD 96. The remaining portions of material of the gate electrodes 102 and the gate dielectric layers 100 thus form replacement gates of the resulting FinFETs. The gate electrodes 102 and the gate dielectric layers 100 may be collectively referred to as "gate stacks." The gate and the gate stacks may extend along sidewalls of the channel regions 68 of the fins 55.

The formation of the gate dielectric layers 100 in the region 50N and the region 50P may occur simultaneously such that the gate dielectric layers 100 in each region are formed from the same materials, and the formation of the gate electrodes 102 may occur simultaneously such that the gate electrodes 102 in each region are formed from the same materials. In some embodiments, the gate dielectric layers 100 in each region may be formed by distinct processes, such that the gate dielectric layers 100 may be different materials, and/or the gate electrodes 102 in each region may be formed by distinct processes, such that the gate electrodes 102 may be different materials. Various masking steps may be used to mask and expose appropriate regions when using distinct processes.

Figure 16B:
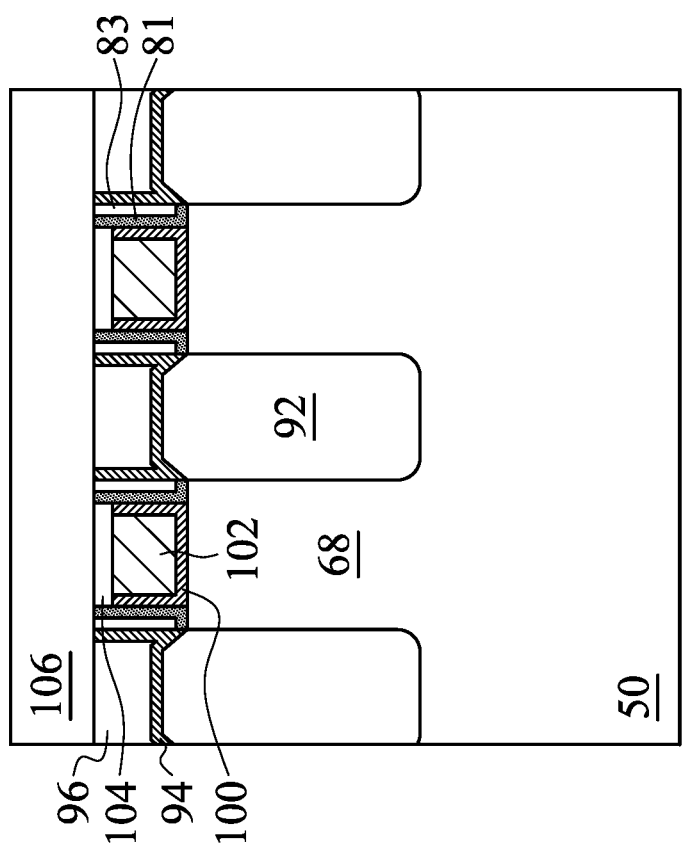
Figure 16A:
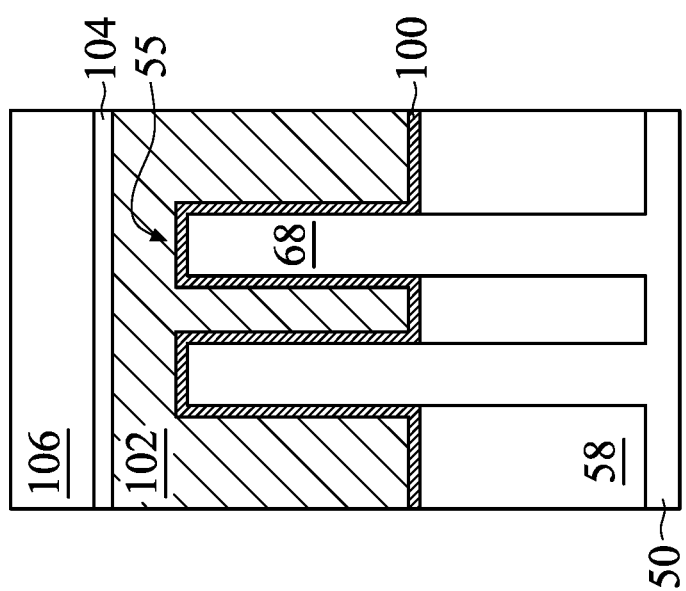

In FIGS. 16A and 16B, a second ILD 106 is deposited over the first ILD 96. In some embodiments, the second ILD 106 is a flowable film formed by FCVD. In some embodiments, the second ILD 106 is formed of a dielectric material such as PSG, BSG, BPSG, USG, or the like, and may be deposited by any suitable method, such as CVD, PECVD, or the like. In some embodiments, before the formation of the second ILD 106, the gate stack (including the gate dielectric layers 100 and the corresponding overlying gate electrodes 102) is recessed, so that a recess is formed directly over the gate stack and between opposing portions of first spacers 81. A gate mask 104 comprising one or more layers of dielectric material, such as silicon nitride, silicon oxynitride, or the like, is filled in the recess, followed by a planarization process to remove excess portions of the dielectric material extending over the first ILD 96. Subsequently formed gate contacts (such as the gate contacts 112, discussed below with respect to FIGS. 17A and 17B) penetrate through the gate mask 104 to contact the top surface of the recessed gate electrodes 102.

In FIGS. 17A-17D, gate contacts 112 and source/drain contacts 114 are formed through the second ILD 106 and the first ILD 96. Openings for the source/drain contacts 114 are formed through the first ILD 96 and the second ILD 106 and openings for the gate contacts 112 are formed through the second ILD 106 and the gate mask 104. The openings may be formed using acceptable photolithography and etching techniques. A liner, such as a diffusion barrier layer, an adhesion layer, or the like, and a conductive material are formed in the openings. The liner may include titanium, titanium nitride, tantalum, tantalum nitride, or the like. The conductive material may be copper, a copper alloy, silver, gold, tungsten, cobalt, aluminum, nickel, or the like. A planarization process, such as a CMP, may be performed to remove excess material from a surface of the second ILD 106. The remaining liner and conductive material form the source/drain contacts 114 and the gate contacts 112 in the openings. An anneal process may be performed to form a silicide at the interface between the epitaxial source/drain regions 92 and the source/drain contacts 114. The source/drain contacts 114 are physically and electrically coupled to the epitaxial source/drain regions 92, and the gate contacts 112 are physically and electrically coupled to the gate electrodes 102. The source/drain contacts 114 and the gate contacts 112 may be formed in different processes, or may be formed in the same process. Although shown as being formed in the same cross-sections, it should be appreciated that each of the source/drain contacts 114 and the gate contacts 112 may be formed in different cross-sections, which may avoid shorting of the contacts.

Figure 17D:
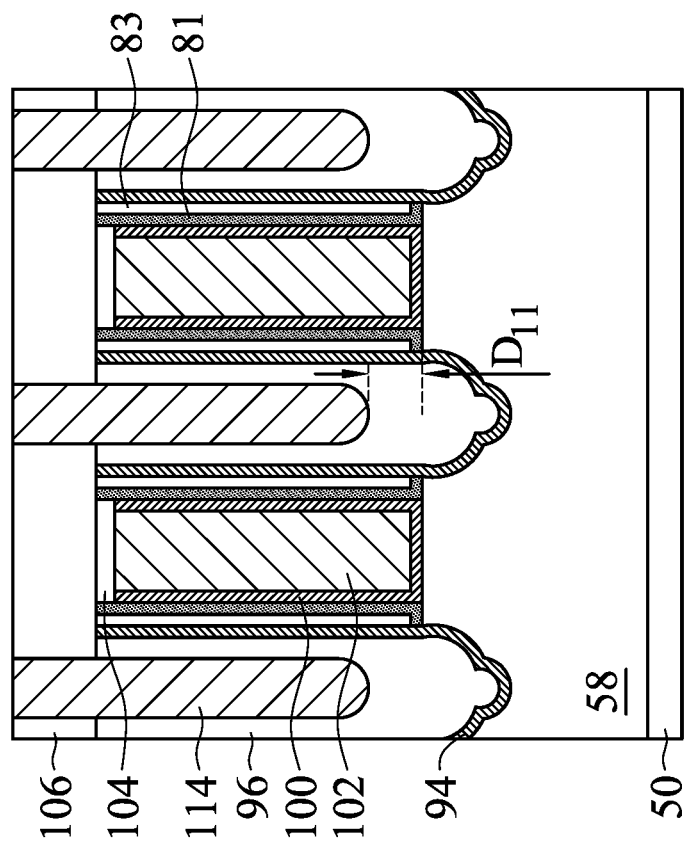
Figure 17C:
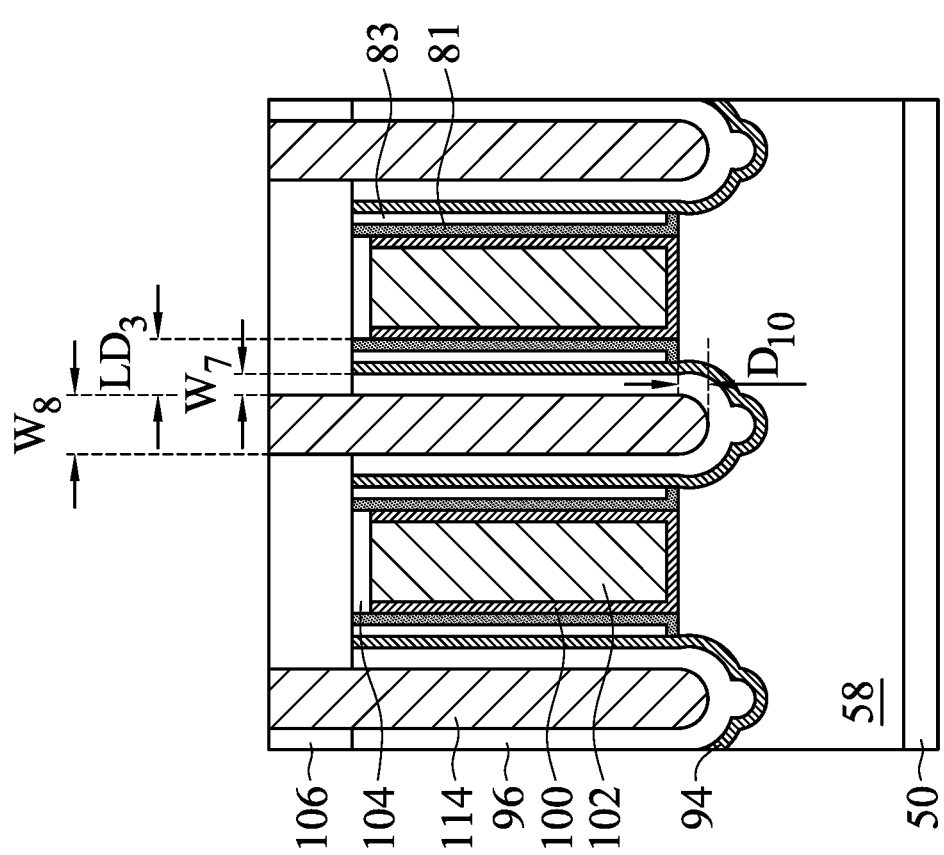

As illustrated in FIG. 17C, the source/drain contacts 114 may extend a distance $D_{10}$ below top surfaces of the STI regions 58 from about 5 nm to about 10 nm or from about 6 nm to about 9 nm. A width $W_7$ of the first ILD 96 extending from a sidewall of the CESL 94 to a sidewall of the source/drain contacts 114 may be from about 5 nm to about 10 nm and a width $W_8$ of the source/drain contacts 114 may be from about 15 nm to about 20 nm. A ratio of the width $W_8$ to the width $W_7$ may be from about 3:1 to about 4:1. As illustrated in FIG. 17D, in some embodiments, bottom surfaces of the source/drain contacts 114 may be disposed above top surfaces of the STI regions 58. For example, the bottom surfaces of the source/drain contacts 114 may be disposed above the top surfaces of the STI regions 58 a distance $D_{11}$ from about 2 nm to about 8 nm or from about 3 nm to about 6 nm. The source/drain contacts 114 may be connected to two or more of the epitaxial source/drain regions 92 and FIGS. 17C and 17D illustrate the source/drain contacts 114 between the epitaxial source/drain regions 92. The source/drain contacts 114 may be separated from the gate stacks by a lateral distance $LD_3$ of at least 6 nm or from about 4 to about 10 nm. Separating the source/drain contacts 114 from the gate stacks by at least the lateral distance helps to increase breakdown voltage, improve device performance, and reduce device defects.

As illustrated in FIGS. 17C and 17D, the first ILD 96 may have substantially straight, vertical sidewall extending from a point level with top surfaces of the gate mask 104, the first spacers 81, and the second spacers 83 to a point level with bottom surfaces of the gate dielectric layers 100, the first spacers 81, and the second spacers 83. The sidewalls of the first ILD 96 may have a first rounded profile extending from the point level with the bottom surfaces of the gate dielectric layers 100, the first spacers 81, and the second spacers 83 to a first depth below top surfaces of the STI regions 58. The first rounded profile may have a first diameter. The sidewalls of the first ILD 96 may have a second rounded profile extending from the first depth to a second depth below the top surfaces of the STI regions 58. The second rounded profile may have a second diameter less than the first diameter. A ratio of the second diameter to the first diameter may be from about 5:6 to about 2:3 or from about 4:5 to about 7:10 and a ratio of the first depth to the second depth may be from about 4:1 to about 7:1 or from about 5:1 to about 6:1. As further illustrated in FIGS. 17C and 17D, sidewalls of upper portions of the source/drain contacts 114 may be substantially straight and vertical and sidewalls of lower portions of the source/drain contacts 114 may have a rounded profile.

As discussed previously, using the above-described pre-clean process and the above-described implanting process on the STI regions 58 reduces material loss from the STI regions 58 and improves the resistance of the STI regions 58, respectively. This helps to increase breakdown voltage, improve device performance, and reduce device defects in semiconductor devices formed according to the above-described processes.

The disclosed FinFET embodiments could also be applied to nanostructure devices such as nanostructure (e.g., nanosheet, nanowire, gate-all-around, or the like) field effect transistors (NSFETs). In an NSFET embodiment, the fins are replaced by nanostructures formed by patterning a stack of alternating layers of channel layers and sacrificial layers. Dummy gate stacks and source/drain regions are formed in a manner similar to the above-described embodiments. After the dummy gate stacks are removed, the sacrificial layers can be partially or fully removed in channel regions. The replacement gate structures are formed in a manner similar to the above-described embodiments, the replacement gate structures may partially or completely fill openings left by removing the sacrificial layers, and the replacement gate structures may partially or completely surround the channel layers in the channel regions of the NSFET devices. ILDs and contacts to the replacement gate structures and the source/drain regions may be formed in a manner similar to the above-described embodiments. A nanostructure device can be formed as disclosed in U.S. Patent Application Publication No. 2016/0365414, which is incorporated herein by reference in its entirety.

In accordance with an embodiment, a method includes forming a shallow trench isolation region over a semiconductor substrate; forming a gate stack over the shallow trench isolation region; etching the shallow trench isolation region adjacent the gate stack using an anisotropic etching process; and after etching the shallow trench isolation region with the anisotropic etching process, etching the shallow trench isolation region with an isotropic etching process, process gases for the isotropic etching process including hydrogen fluoride (HF) and ammonia ($NH_3$). In an embodiment, a flowrate of hydrogen fluoride during the isotropic etching process is from 2 sccm to 7 sccm and a flowrate of ammonia during the isotropic etching process is from 6 sccm to 20 sccm. In an embodiment, a ratio of a flowrate of ammonia to a flowrate of hydrogen fluoride during the isotropic etching process is from 3:1. In an embodiment, the anisotropic etching process etches the shallow trench isolation region to a depth below a top surface of the shallow trench isolation region from 5 nm to 25 nm, and the isotropic etching process etches the shallow trench isolation region to a depth below the top surface of the shallow trench isolation region from 10 nm to 30 nm. In an embodiment, the method further includes implanting an impurity into the shallow trench isolation region after etching the shallow trench isolation region with the isotropic etching process. In an embodiment, the impurity includes phosphorous, and the shallow trench isolation region is doped to phosphorous concentration of at least $1\times10^{15}$ atoms/cm$^3$. In an embodiment, the shallow trench isolation region is etched with the isotropic etching process for 70 seconds to 80 seconds. In an embodiment, etching the shallow trench isolation region using the anisotropic etching process forms a first rounded profile in the shallow trench isolation region to a depth below a top surface of the shallow trench isolation region from 5 nm to 25 nm, and etching the shallow trench isolation region with the isotropic etching process forms a second rounded profile in the shallow trench isolation region to a depth below the top surface of the shallow trench isolation region from 5 nm to 25 nm and a third rounded profile in the shallow trench isolation region extending from the second rounded profile to a depth below the top surface of the shallow trench isolation region from 10 nm to 30 nm.

In accordance with another embodiment, a method includes forming a gate stack over a semiconductor fin, the semiconductor fin extending from a semiconductor substrate; anisotropically etching the semiconductor fin to form a first recess; and isotropically etching the semiconductor fin to remove an oxide from the semiconductor fin using a plasma-less, dry etching process. In an embodiment, isotropically etching the semiconductor fin includes exposing the semiconductor fin to a process gas including hydrogen fluoride (HF) and ammonia (NH$_3$). In an embodiment, a ratio of a flowrate of ammonia in the process gas to a flowrate of hydrogen fluoride in the process gas is 3:1. In an embodiment, a flowrate of ammonia in the process gas is from 6 sccm to 20 sccm and a flowrate of hydrogen fluoride in the process gas is from 2 sccm to 7 sccm. In an embodiment, the method further includes epitaxially growing a source/drain region in the first recess after isotropically etching the semiconductor fin.

In accordance with yet another embodiment, a semiconductor device includes a shallow trench isolation (STI) region over a semiconductor substrate; a gate electrode over the STI region; and a first dielectric over the STI region and surrounding the gate electrode, the first dielectric having a first rounded profile extending below a top surface of the STI region a first distance from 5 nm to 25 nm, the first dielectric having a second rounded profile extending from the first rounded profile below a top surface of the STI region a second distance from 10 nm to 30 nm. In an embodiment, the semiconductor device further includes a gate spacer adjacent the gate electrode, the first dielectric extending under the gate spacer a lateral distance from 3 nm to 5 nm. In an embodiment, the STI region is doped with phosphorous. In an embodiment, the STI region is doped with phosphorous to a dopant concentration of at least $1\times10^{15}$ atoms/cm$^3$. In an embodiment, the first rounded profile has a maximum width from 25 nm to 30 nm, and the second rounded profile has a maximum width from 5 nm to 10 nm. In an embodiment, the first dielectric includes a contact etch stop layer (CESL) and an interlayer dielectric (ILD) over the CESL. In an embodiment, the semiconductor device further includes a source/drain contact extending at least partially through the first dielectric, a bottom surface of the source/drain contact being disposed below a top surface of the STI region.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method comprising:
    forming a shallow trench isolation region over a semiconductor substrate;
    forming a gate stack over the shallow trench isolation region;
    etching the shallow trench isolation region adjacent the gate stack using an anisotropic etching process, wherein etching the shallow trench isolation region using the anisotropic etching process forms a first rounded profile in the shallow trench isolation region to a first depth below a top surface of the shallow trench isolation region; and
    after etching the shallow trench isolation region with the anisotropic etching process, etching the shallow trench isolation region with an isotropic etching process, wherein process gases for the isotropic etching process comprise hydrogen fluoride (HF) and ammonia (NH3), wherein etching the shallow trench isolation region with the isotropic etching process forms a second rounded profile in the shallow trench isolation region to the first depth below the top surface of the shallow trench isolation region and a third rounded profile in the shallow trench isolation region extending from the second rounded profile to a second depth below the top surface of the shallow trench isolation region.

2. The method of claim 1, wherein a flowrate of hydrogen fluoride during the isotropic etching process is from 2 sccm to 7 sccm and a flowrate of ammonia during the isotropic etching process is from 6 sccm to 20 sccm.

3. The method of claim 1, wherein a ratio of a flowrate of ammonia to a flowrate of hydrogen fluoride during the isotropic etching process is 3:1.

4. The method of claim 1, wherein the anisotropic etching process etches the shallow trench isolation region to a depth below a top surface of the shallow trench isolation region from 5 nm to 25 nm, and wherein the isotropic etching process etches the shallow trench isolation region to a depth below the top surface of the shallow trench isolation region from 10 nm to 30 nm.

5. The method of claim 1, further comprising implanting an impurity into the shallow trench isolation region after etching the shallow trench isolation region with the isotropic etching process.

6. The method of claim 5, wherein the impurity comprises phosphorous, and wherein the shallow trench isolation region is doped to phosphorous concentration of at least 1×1015 atoms/cm3.

7. The method of claim 1, wherein the shallow trench isolation region is etched with the isotropic etching process for 70 seconds to 80 seconds.

8. The method of claim 1, wherein the first depth is from 5 nm to 25 nm, and wherein the second depth is from 10 nm to 30 nm.

9. A method comprising:
forming an isolation region over a semiconductor substrate and adjacent a semiconductor fin, the semiconductor fin extending from the semiconductor substrate;
forming a gate stack over the semiconductor fin and the isolation region;
anisotropically etching the semiconductor fin and the isolation region, wherein anisotropically etching the semiconductor fin removes material of the semiconductor fin and forms a first recess in the semiconductor fin; and
isotropically etching the semiconductor fin and the isolation region, wherein isotropically etching the semiconductor fin removes a native oxide from inner surfaces of the first recess using a plasma-less, dry etching process, wherein isotropically etching the semiconductor fin comprises exposing the semiconductor fin to a process gas comprising hydrogen fluoride (HF) and ammonia (NH3).

10. The method of claim 9, wherein a ratio of a flowrate of ammonia in the process gas to a flowrate of hydrogen fluoride in the process gas is 3:1.

11. The method of claim 9, wherein a flowrate of ammonia in the process gas is from 6 sccm to 20 sccm and a flowrate of hydrogen fluoride in the process gas is from 2 sccm to 7 sccm.

12. The method of claim 9, further comprising epitaxially growing a source/drain region in the first recess after isotropically etching the semiconductor fin.

13. The method of claim 9, wherein anisotropically etching the semiconductor fin to form the first recess comprises exposing the semiconductor fin to a process gas comprising hydrogen bromide (HBr), methane (CH4), and helium (He).

14. A method comprising:
forming a shallow trench isolation region over a semiconductor substrate;
forming a gate stack over the shallow trench isolation region;
etching the shallow trench isolation region adjacent the gate stack using an anisotropic etching process;
etching the shallow trench isolation region with an isotropic etching process, wherein process gases for the isotropic etching process comprise hydrogen fluoride (HF) and ammonia (NH3); and
forming a first dielectric over the shallow trench isolation region and surrounding the gate stack, the first dielectric having a first rounded profile extending below a top surface of the shallow trench isolation region a first distance from 5 nm to 25 nm, the first dielectric having a second rounded profile extending from the first rounded profile below the top surface of the shallow trench isolation region a second distance from 10 nm to 30 nm.

15. The method of claim 14, wherein forming the gate stack comprises:
forming a gate electrode; and
forming a gate spacer adjacent the gate electrode, wherein the first dielectric extends under the gate spacer a lateral distance from 3 nm to 5 nm.

16. The method of claim 14, further comprising doping the shallow trench isolation region with phosphorous.

17. The method of claim 16, wherein the shallow trench isolation region is doped with phosphorous to a dopant concentration of at least $1 \times 10^{15}$ atoms/cm3.

18. The method of claim 14, wherein the first rounded profile has a maximum width from 25 nm to 30 nm, and wherein the second rounded profile has a maximum width from 5 nm to 10 nm.

19. The method of claim 14, wherein forming the first dielectric comprises
depositing a contact etch stop layer (CESL) over the shallow trench isolation region; and
depositing an interlayer dielectric (ILD) over the CESL.

20. The method of claim 14, further comprising forming a source/drain contact extending at least partially through the first dielectric, wherein a bottom surface of the source/drain contact is disposed below a top surface of the shallow trench isolation region.

* * * * *